(12) United States Patent
Fischell et al.

(10) Patent No.: US 8,676,304 B2
(45) Date of Patent: Mar. 18, 2014

(54) ISCHEMIA MONITORING SYSTEM FOR PATIENTS HAVING PERIODS OF LEFT BUNDLE BRANCH BLOCK

(75) Inventors: David R. Fischell, Fair Haven, NJ (US); Bruce Hopenfeld, Salt Lake City, UT (US); Michael Sasha John, Larchmont, NY (US); David Keenan, Tinton Falls, NJ (US)

(73) Assignee: Angel Medical Systems, Inc., Fair Haven, NJ (US)

( * ) Notice: Subject to any disclaimer, the term of this patent is extended or adjusted under 35 U.S.C. 154(b) by 664 days.

(21) Appl. No.: 12/791,327

(22) Filed: Jun. 1, 2010

(65) Prior Publication Data
US 2011/0125041 A1    May 26, 2011

Related U.S. Application Data

(63) Continuation-in-part of application No. 12/624,506, filed on Nov. 24, 2009, now Pat. No. 8,452,404.

(51) Int. Cl.
*A61B 5/02* (2006.01)
*A61B 5/04* (2006.01)
*A61N 1/00* (2006.01)

(52) U.S. Cl.
USPC ............ 600/509; 600/508; 600/515; 600/516; 600/517; 600/518; 607/4; 607/5; 607/9; 607/14

(58) Field of Classification Search
USPC .................. 600/373, 374, 481, 508, 509, 512, 600/515–519, 521; 607/18, 25, 119, 4, 5, 9, 607/14
See application file for complete search history.

(56) References Cited

U.S. PATENT DOCUMENTS

| | | | |
|---|---|---|---|
| 6,112,116 A | 8/2000 | Fischell et al. | |
| 6,272,379 B1 | 8/2001 | Fischell et al. | |
| 6,609,023 B1 | 8/2003 | Fischell et al. | |
| 2005/0010120 A1* | 1/2005 | Jung et al. | 600/509 |

* cited by examiner

*Primary Examiner* — Niketa Patel
*Assistant Examiner* — Lindsey G Hankins
(74) *Attorney, Agent, or Firm* — Rosenberg, Klein & Lee

(57) ABSTRACT

A device for detecting cardiac ischemia is disclosed. The device includes a processor that is configured to distinguish between two different heart beats types such as left bundle branch block beats and normal sinus beats. The processor applies different ischemia tests to the two different beat types, and generates alert when it detects ischemia.

20 Claims, 17 Drawing Sheets

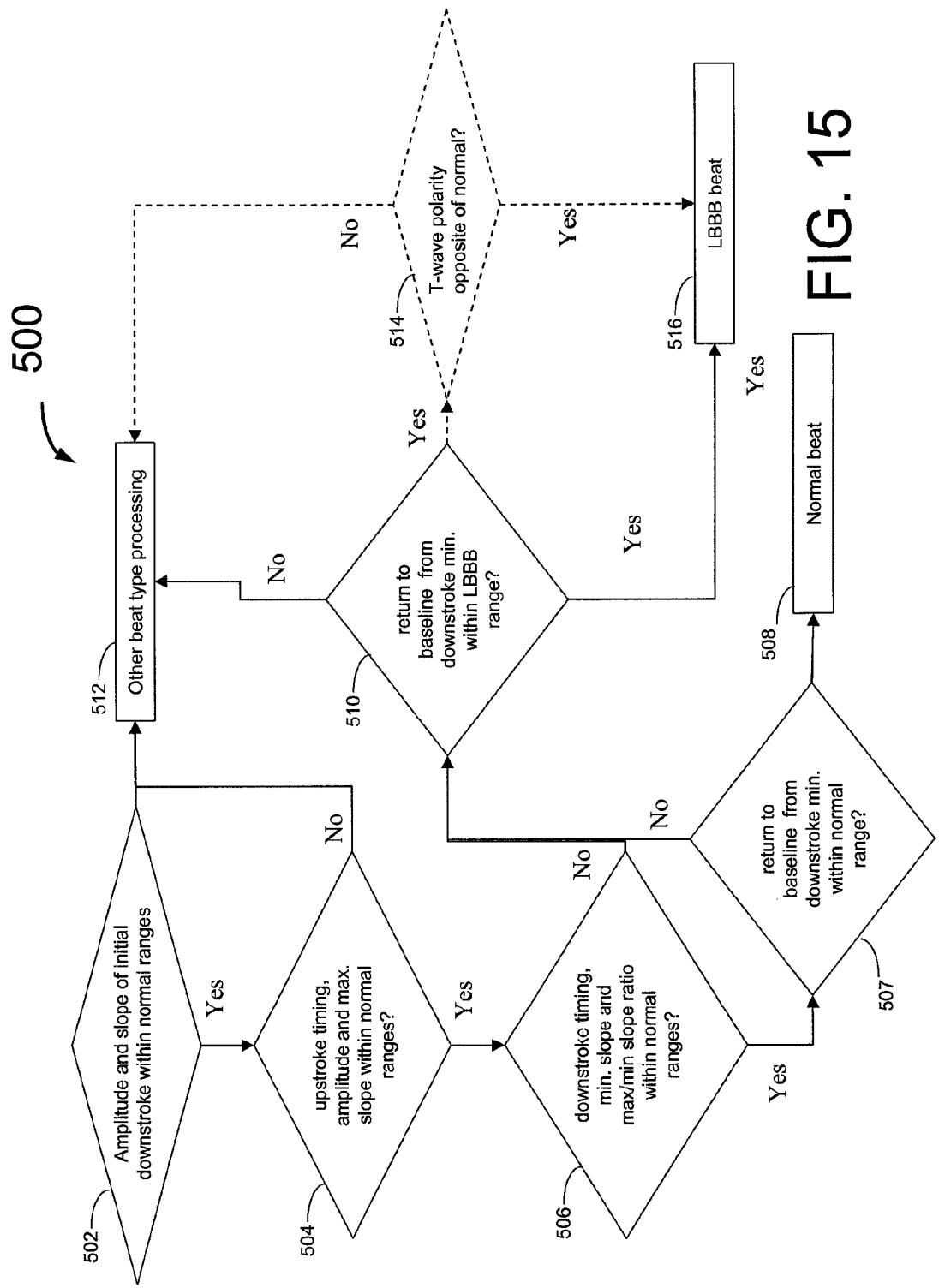

ISCHEMIA MONITORING SYSTEM FOR PATIENTS HAVING PERIODS OF LEFT BUNDLE BRANCH BLOCK

REFERENCE TO RELATED APPLICATIONS

This Application is being filed as a Continuation-in-Part of patent application Ser. No. 12/624,506, filed 24 Nov. 2009, currently pending.

FIELD

The invention is in the field of cardiac diagnostic devices and implantable cardiac pacemakers and resynchronization devices.

BACKGROUND

Implantable medical devices (IMD) that can alert patients or third parties to the detection of ischemic events including heart attacks (Myocardial Infarction) can save lives and reduce damage to a patient's heart tissue, improving the post-myocardial-infarction quality of life. Myocardial infarction (MI) occurs when a blood clot blocks the blood supply to a portion of the heart causing the heart tissue to become hypoxic (ischemic) and also experience decreased metabolite removal. Ischemia detection may occur by analysis of the patient's cardiac activity, especially via electrical waveforms sensed by electrodes.

The combination of a pacemaker or ICD with an ischemia detector is described by Fischell et al in U.S. Pat. Nos. 6,112, 116, 6,272,379 and 6,609,023. Fischell describes an IMD which can detect a change in the electrical signal from the patient's heart (cardiac electrical signal) that is indicative of a cardiac event, such as an acute ischemia, and then provide a notification of such an event. The IMD can also be a medical device which senses and/or stimulates cardiac, neural, vagal-nerve, or other anatomical target in order to control cardiac activity. Fischell also describes an external alarm system that can provide additional visual, sonic and vibratory alerting signals and may also provide voice/data communication between the IMD and a remote medical monitoring station.

Fischell et all in the above mentioned patents primarily uses changes in the ST segment of the electrogram as the primary indicator of ischemia. Unfortunately, the intracardiac electrogram seen during episodes of left bundle branch block (LBBB) often exhibit significant ST changes that could be misinterpreted as an ischemic event. A helpful characteristic of the LBBB electrogram signal is a significant widening of the QRS complex. Fischell et al do not describe a specific scheme for performing ischemia detection in a patient that experiences both normal and LBBB beats.

SUMMARY

Systems and methods for monitoring ischemia in a patient who, at least sporadically, has periods of left bundle branch block are described. Ischemia monitoring can lead to notification of the patient or a third party when certain events occur. Events may include, for example, measuring an abnormal level of ischemia in left bundle branch heart-beats, normal sinus heartbeats, or both.

LBBB beats can be identified by an immediate widening of the QRS complex, in conjunction with other specific beat morphology characteristics, as compared to normal sinus beats.

In one embodiment of the current invention, the choice of measured features for each heart beat, are different as a function of beat type for the sinus and LBBB heartbeats. Alternatively, the measured features for each heart beat are the same for both beat types, but the measurement protocol for deriving each feature varies according to beat type. Further, assessment of ischemia is contingently adjusted based upon beat type. When segment-based ischemia detection as described by Fischell in U.S. Pat. No. 6,609,023 is utilized, the number of segments, or other segment-based criteria used to determine if ischemia-related alerting should occur can vary according to the composition of beat types (e.g. proportion of each type of beat) distributed within the segments.

In another aspect, reference values and baseline data to which current beats are compared are operated upon as a function of beat type. Baseline data may be collected at particular intervals or times or in relation to periods of LBBB.

In another aspect the period of ischemia monitoring is contingently delayed, aborted, extended or otherwise adjusted based upon the beat type being seen. Adjustment of monitoring can also occur in relation to what baseline data is available for a particular beat type. Adjustment of monitoring can include increasing the amount of time that sensing occurs so that instead of monitoring N of every M seconds, for example, monitoring may be extended to the full M seconds until a sufficient amount of acceptable data is obtained to monitor ischemia.

In another aspect the ischemia monitoring may be adjusted based upon the occurrence, or anticipation, of LBBB which may be inferred from the analysis of cardiac data which is sensed.

In another aspect the implantable ischemia monitor may contain a pacing system that delivers pacing pulses or a defibrillation system that can deliver defibrillation shocks. In another aspect the monitor may be used in a patient where the pacing is provided by an independently operated pacemaker, which may or may not be configured to cooperate or communicate with the ischemia monitoring device.

In another aspect, device operation including, for example, the measurement of beat features, assessment of features in relation to ischemia, baseline and reference data collection, and alerting operations, can be adjusted in relation to current or historical presence of sinus and LBBB beat types. In a further aspect, the monitoring device contains a pacing module which contains the ability to operate upon sensed cardiac data to determine if pacing should be provided and to operate a stimulation subsystem to provide pacing according to a pacing protocol. The parameters of the pacing protocol may be further modified according to the ischemia detection operations and monitoring operations, and vice-versa. Techniques for ischemia monitoring on LBBB and normal sinus beat types is described by Fischell et al in U.S. patent application Ser. Nos. 12/624,496, 12/624,506, 12/624,515 and 12/624,521

Lastly, in one embodiment, the present invention classifies three modes of ischemia monitoring based on the amount of LBBB seen in the patient's heart signal. The first is a mode that is oriented for ischemia monitoring when LBBB is extremely rare. The second mode is used when LBBB is continuous and sinus rhythms are rare. The third mode is used when there are relatively frequent intervals of both sinus and LBBB beats. Further, the mode which is used can be programmed by a doctor or can be adaptively selected by the device based upon the history of Left Bundle Branch Block of the patient as recorded in the device's memory.

The primary functionality of the present invention has ischemia detection capability for both sinus and LBBB beats, can identify the prevalence of LBBB beats for the patient and consequently select one of the ischemia monitoring modes listed above and operates as follows for each mode.

In the case of mode 1, LBBB beats are rare and occur typically only for a short time, e.g. less than 10 minutes at a time and less than an hour a day. When LBBB beats are rare, the primary ischemia detection technique is to process only normal sinus beats and ignore LBBB beats. Because any real ischemic event such as a heart attack from a blocked coronary artery will produce electrogram or electrocardiogram changes that may last for tens of minutes or even hours, ignoring a small number of LBBB beats will not create significant delays in detection and alerting.

For mode 2 where LBBB beats are pretty much continuous, one can ignore sinus beats when they occur.

For mode 3 the present invention must separately run detection algorithms for both LBBB and normal sinus beats so that it can identify an ischemic event either from a single beat type or by sufficient changes in both beat types using detection protocols having any of the following: different detection criteria, different algorithms for detection and/or different thresholds for detection. In this mode there would typically be more than 30 minutes a day of both LBBB and normal sinus beats with episodes of both LBBB and normal sinus beats that exceed 10 minutes. One significant aspect of the present invention pertains to mode 3 detection and deciding when to transition the ischemia detection scheme between modes, such as from mode 1 or mode 2 to mode 3.

One embodiment of the present invention uses an ischemia detection algorithm such as that of Fischell in U.S. Pat. No. 6,069,023 where calculated heart signal parameters from newly collected beats of the heart signal are compared to baseline data collected at a prior time period when the heart signal was "normal". An aspect of this algorithm is the collection of this baseline heart signal parameter data during "normal" heart activity. In this embodiment the present invention can decide to process beats of the heart signal to extract baseline heart signal parameter data whenever the signal has a sufficiency of "normal" beats over a period of time, for example at least 10 normal sinus beats over a 5 minute period. Similarly it can process LBBB beats to extract baseline heart signal parameter data for LBBB beats if the signal has a sufficiency of LBBB beats over a period of time, for example at least 10 LBBB over a 5 minute period. The baseline data for LBBB and normal sinus beats can be collected periodically (e.g. once an hour) and averaged together over a longer period (e.g. a day) to create the baseline data against which the heart signal parameter data of new beats are compared. Heart signal parameters for new LBBB beats are compared to the LBBB beat baseline data and heart signal parameters for normal sinus are compared to the normal sinus baseline data.

It is envisioned that if an insufficient number of normal sinus beats occur over a period of time, the algorithm can revert to mode 2 and ignore normal sinus beats until there are enough to establish a new baseline. Alternately this can occur when the baseline data for normal sinus beats becomes too old (e.g. has had no new data added for 3 days). Until then the old baseline may still be used.

A similar technique can also be used if there is an insufficiency of LBBB beats where the algorithm would revert to mode 1 and ignore LBBB beats until there is a sufficiency to establish a new baseline Another feature of the present invention involves the selective application of time rate of change information to test for ischemia. Time rate of change ischemia tests are disclosed in U.S. patent application Ser. No. 11/898,673, filed September 2007, entitled "Waveform Feature Value Averaging System and Methods for the Detection of Cardiac Events", and owned by the assignee hereof; and U.S. provisional patent application 61/152,367, filed February 2009, entitled "Time Series Tracking System and Methods for the Detection of Cardiac Events", filed February 2009 and owned by the assignee hereof, and U.S. patent application Ser. No. 12/461,442 entitled "Heart Rate Correction System and Methods for the Detection of Cardiac Events", filed August 2009 and owned by the assignee hereof (collectively, "Rate of Change Applications") The present invention separately examines LBBB and normal sinus beats, calculate the time rate of change separately for each, and compare the rate of change with separate detection thresholds. It is also envisioned in this embodiment, the heart signal parameter(s) could be different or could be calculated differently for LBBB vs. normal sinus beats. For example, the time rate of change of ST segment voltage could be used for normal sinus beats while the time rate of change of QT time could be used for LBBB beats. It is also envisioned that the system can be examining the time rate of change of more than one heart signal parameter for either or both LBBB and normal sinus beats. For example, time rate of change of ST voltage could be used for normal sinus beats and both time rate of change of ST voltage and QT time could be used for LBBB beats or vice versa. It is also envisioned that the location of the ST segment or other heart signal features in relation to the R wave or another reference heart signal feature can be determined differently for LBBB and normal sinus beats. Since LBBB beats have a wider QRS width than normal sinus beats, it is envisioned that the ST segment for LBBB beats occurs later after the R wave than for normal sinus beats. For example the ST segment might for a 60 bpm heart rate be 30 ms long and 50 ms after the R wave for a normal sinus beat and 20 ms long and 70 ms after the R wave for a paced beat.

The described invention addresses the shortcomings of medical ischemia monitoring systems that do not monitor, adjust in response to, or compensate for the occurrence of left bundle branch block. Additionally, the invention provides the advantage of adjusting ischemia detection parameters based upon the types of beats which are present in cardiac data in order to more accurately provide ischemia monitoring and detection of medically relevant ischemic events.

Thus it is an object of the present invention to have an ischemia detection system capable of identifying changes in the heart signal indicating left bundle branch block and applying appropriate ischemia detection rules based the identification.

Another object of the present invention is to ignore LBBB beats if the primary mode is one in which LBBB beats are rare.

Still another object of the present invention is to ignore normal sinus beats if the primary mode is one in which left bundle branch block is continuous.

Still another object of the present invention is in the case of significant numbers of both LBBB and normal sinus beats to separately process each beat, applying different ischemia detection criteria to each type of beat.

Yet another object of the present invention is to identify an acute ischemic event based on a sufficient change in either LBBB or normal sinus beats.

Yet another object of the present invention is to be able to identify an acute ischemic event based on a combination of changes in both LBBB and normal sinus beats.

These and other objects and advantages of this invention will become obvious to a person of ordinary skill in this art upon reading of the detailed description of this invention including the associated drawings as presented herein.

BRIEF DESCRIPTION OF THE FIGURES

FIG. 15 shows steps of a method used to classify beats as normal beats, LBBB beats or other type beats.

DETAILED DESCRIPTION OF THE INVENTION

Figure 1:
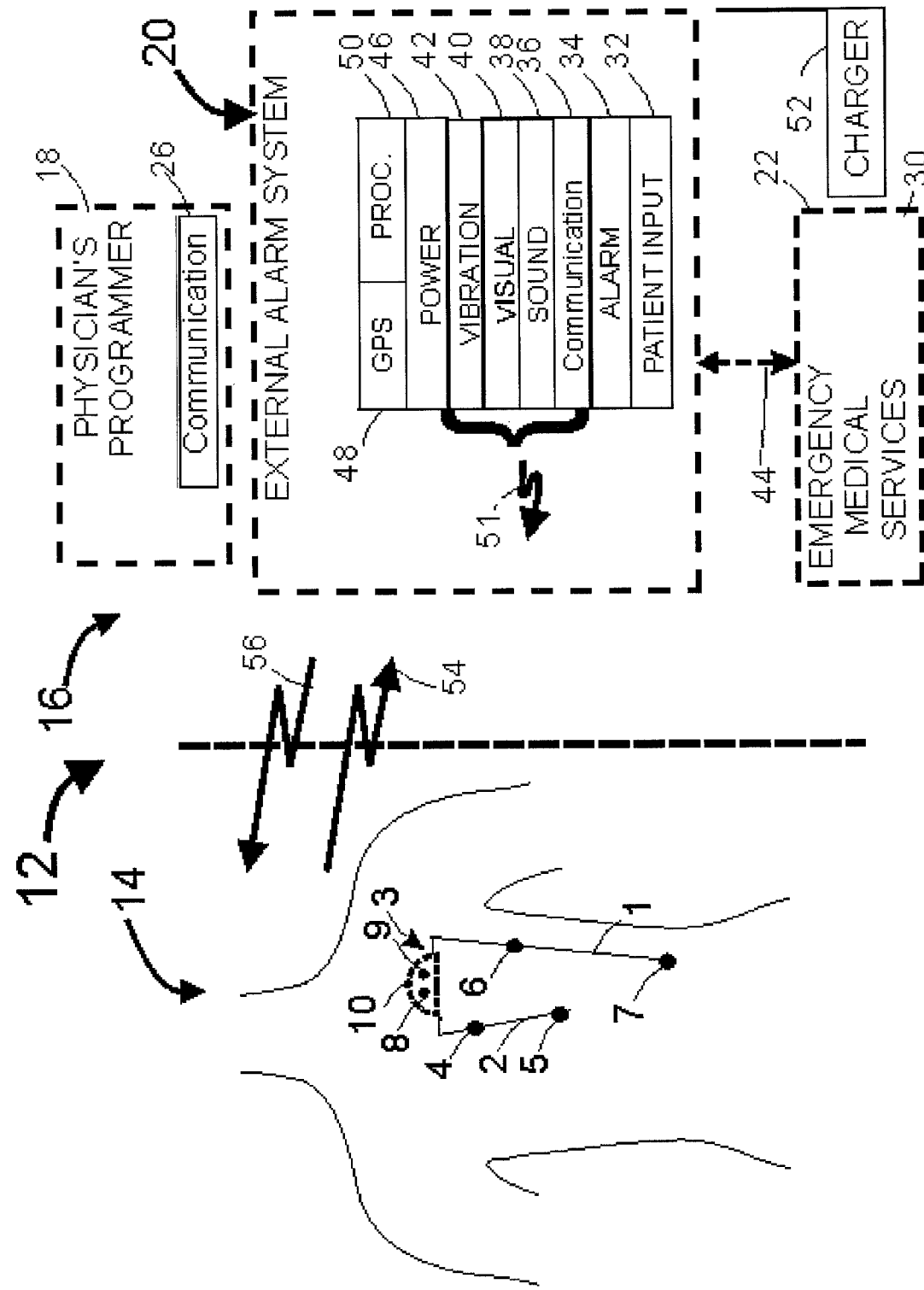
FIG. 1 shows a system which uses a single device having both ischemia monitoring and pacing capability.

FIG. 1 illustrates an example of a medical system 12 including implanted components 14 and external equipment 16. The implantable medical device (IMD) 3 includes sensors to monitor a cardiac condition associated with a patient. Electrode sensors can measure cardiac activity, neural activity, vagal activity, respiratory activity or other electrical activity which can influence cardiac function and demand. A microphone sensor can measure sonic data related to the patient (e.g. cardiac or respiratory sounds), an accelerometer can measure movement, acceleration or position, and a biosensor can measure metabolite levels within the patient. In one embodiment, sensors include the electrodes 4 and 5 incorporated into an insulated electrical wire lead 2. The lead 2 is electrically connected with the IMD 3. Through this connection the IMD that includes battery-powered sensing electronics receives signals from the electrodes 4 and 5. The connection may be of a custom design or preferably use a standardized pacemaker connector such as an IS1. The lead 2 with electrodes 4 and 5, can be placed subcutaneously, epicardially or within the heart. It is also that the lead 2 could have only one electrode or a many as sixteen. When multiple electrodes are used, the cardiac features for the beats sensed in the data from each electrode may be measured using a protocol specific to each electrode. Further, baseline (historical self-norm) data may be collected and analyzed for each electrode and ischemia detection thresholds may be defined for data sensed at each electrode. During ischemia monitoring the data from each electrode can be evaluated using multivariate methods, where data from each electrode is evaluated to produce an ischemia score, or the data may be combined using "and" or "or" logic by the ischemia detection algorithm. The implantable cardiac monitoring device can include a set of leads which are referenced to each other or to the case 10 of the IMD 3. In a preferred embodiment, the lead 2 is situated with the electrode 5 attached to the endocardium at the right apex of the patient's heart. In an alternative embodiment the electrodes 4 and 5 may be embedded under the patients skin, or may be any combination of implanted intracardiac and extracardiac locations in order to collect cardiac data both within and external to the heart. The lead 1 includes sensors 6 and 7. The sensors 6 and 7 may be additional intracardiac or extracardiac electrodes, microphones, optical sensors, accelerometers, or may be biosensors or chemical sensors that detect the presence or concentration of a biological substrate, medication, or metabolite. The lead 1 connects to the IMD3 providing signals from the patient's body produced by the sensors 6 and 7.

IMD case sensors 8 and 9 could be situated within surface of the case 10 without any wire leads extending from the IMD 3. The case 10 which is typically a thin metal can constructed from a titanium can also serve as a sensing electrode providing electrode-to-can or can-to-electrode sensing for the electrodes 4 and 5, by being connected to one end of a differential amplifier circuit in the sensing electronics of the IMD 3. The IMD 3 may also include pacing electronics designed to electrically stimulate the patient's heart in an currently known form of pacing including single chamber pacing, dual chamber pacing, fixed rate pacing, variable rate pacing, AV pacing and cardiac resynchronization (CRT). The IMD 3 can provide pacing through the electrodes 4 and 5 of the lead 2, through the electrodes 6 and 7 of the second lead 1, both leads or a third lead (not shown). When sensors 4, 5, 6, 7, 8, and 9 are all electrodes, these can be configured with respect to the stimulation and sensing subsystems of the IMD 3 in order to provide stimulation, sensing, or both. Electrical stimulation, for example, using electrodes 8 and 9 which may stimulate referenced to each other or to the can 10, can also be used to provide an electric tickle for alerting purposes. In one embodiment the lead 2 in FIG. 1 could contain a sensor 5 that is advantageously placed through the patient's vascular system and into the apex of the right ventricle in order to monitor cardiac activity. When the lead 2 contains a sensor 5 such as a pressure or optical sensor, the lead 2 will have multiple conductive pathways for providing power to the sensor 5 and receiving data from the sensor 5.

FIG. 1 also shows external equipment 16 designed to communicate with the IMD 3 that may include: 1. a physician's programmer 18; 2. an external alarm system (EXD) 20 which may be implemented as one or more of a pager-type device, a cell phone or PDA type device or a desktop unit; and, 3. a remote monitoring center 22. The physician's programmer 18 has 2-way wireless communication 26, with antenna, for communication between the programmer 18, the IMD 3 and the EXD 20. The EXD 20 includes a communication module 36 having one or more antenna for wireless communication with the IMD 3, Physician's Programmer 18 and remote monitoring center 22. The Physician's Programmer 18 provides users with the capability of interacting with the IMD 3, for operations including programming and retrieving data from the IMD 3. The EXD 20 also provides external alarm signals for alerting the patient and allows two way wired or wireless communications with the remote monitoring center 22. The remote monitoring center 22 can be one or more third parties including a monitoring service, the patient's doctor, or other intended target.

The programmer 18 shown in FIG. 1 can be used to communicate with the IMD 3 in order to adjust operational parameters related to, for example, pacing protocols and parameters, data collection, measurement of cardiac features in sensed data, event detection, data storage, and alerting protocols. Communication can include wireless signals 56 sent from the programmer 18 communications module 26 to the IMD 3 and or incoming wireless signals 54 sent from the IMD 3 to the communications module 26 of the programmer 18. The programmer 18 functionality related to monitoring of ischemia. For example, the programmer 18 can be configured to adjust parameters used to measure features of LBBB and normal sinus beats, and adjust criteria used to assess these features in relation to ischemia. For example, the programmer 18 also has software routines that provide the medical professional with an interactive graphical display for viewing and or measuring LBBB beats, such as setting start and stop times for the measurements of ST-segments of LBBB and normal sinus beats. Further, the displays can be used to adjust thresholds used for determining ischemia in these two different beat types (e.g., see FIGS. 5A-5C).

In FIG. 1, the EXD 20 has a patient input module 32 which contains a series of physical controls such a buttons. A "patient initiate" button can allow for the initiation of communication between the EXD 20 and the IMD 3. An "alarm disable" button can be used to cause an alarm of the IMD 3 and/or EXD 20 to halt rather than repetitively and needlessly re-alerting a patient. A "panic" button can allow a patient to send an alarm with or without attached data from the IMD 3 to a remote monitoring center 22, even in the absence of IMD 3 or EXD 20 alarm notification. An "event" button can allow patients to tag events and thereby cause data to be tagged and/or sent remotely. An alarm module 34 can operate the communication module 36, sound module 38, visual module 40, and vibration module 42, to create an alarm signal 51 that comprises at least one of: communicating with a $3^{rd}$ party, a sonic alarm, a visual alarm, and a vibration alarm, respectively.

The communication module 36, with the one or more antennae, provides near-field and far-field wireless communication. The near-field communication may use inductively coupled wake-up type communication methods such as are well known while medium and far-field communication may rely upon other means. The communication module 36 can employ standardized wireless methods such as Bluetooth, WiFi, the FCC medical band, and/or cellular communications system such as GSM, CDMA, TDMA. The communication module 36 allows for data and/or voice transmission to and from the medical monitoring center 22 via the communication link 44, and also allows communication with the IMD 3 and programmer 18. The sound module 38 has both sound input and output such as a microphone, and speaker, respectively and associated electronics for providing two-way voice communication with the remote monitoring center 22. Examples of external auditory alarm signals 51 include a periodic buzzing, a sequence of tones and/or speech which may be a pre-recorded message that instructs the patient as to what is happening and what actions should be taken or which may be real speech communicated by the remote monitoring center 22. The visual module 40 can include 1 or more colored diodes which are activated continuously, periodically, or according to a pattern that is associated with a particular alarm type. The visual module 40 may also include a display screen for displaying waveforms, pictures, and text related to system parameters, alarm information, or information related to pacing or ischemia monitoring. Patients may use navigation buttons provided by the patient input module 32 in order to navigate through menus presented on the display of the visual module 40 and to select desired menu options. Alternatively, the display of the visual module 40 may have a touch sensitive display that allows for patient input. The vibration module 42 can contain a vibration motor to produce the vibration alarm signal component of the alarm signal 51, and can also contain an accelerometer which can be used to test the vibration alarm and also to measure a patient's physical activity level when the EXD 20 is worn by the patient.

The processing module 50 of the EXD 20 contains a real time clock or timer and other components which are normally available in the processing modules of current art portable smart-devices and pagers. Further, in a preferred embodiment, the EXD 20 is realized using a smart-phone (e.g., an iPhone, Blackberry or Palm), which may, if necessary, be implemented using specialized software and/or smartcards including means for wireless communication with the IMD 3. The alarm module 34, as well as the other modules of the EXD 20, may be implemented in hardware or software and contains all of the necessary components to implement alarming of the patient and/or remote station. The alarm module 34 collaborates with the processor module 50 to provide alerting by providing instructions to the processor or by receiving commands from the processor which cause it to implement alerting as defined in the alarm protocols, or both.

If an alarm notification is sent from the IMD 3 to the EXD 20, via the 2 way communication modules 36,124 then the alarm module 34 can alert the patient, alert a $3^{rd}$ party, or no alarm may be provided and the EXD 20 is simply operated to send data to a 3rd party for evaluation or storage. When the detection of a life threatening event (e.g., AMI or arrhythmia) is the cause of the alarm, the EXD 20 could automatically notify remote monitoring center 22 that a serious medical condition has occurred, an ambulance could be sent to treat the patient and to bring him to a hospital emergency room or directly to a catheterization laboratory.

If communication with remote monitoring center 22 occurs, then the message sent over the link 44 may include at least one of the following types of information as previously stored in the memory provided within the EXD's processor module 50 or as directly uploaded from the IMD 3: (1) What type of medical event has occurred, (2) the patient's name, address and a brief medical history, (3) a GPS coordinate and/or directions to where the patient is located (using the GPS satellite or cellular grid information as per GPS module 48), (4) patient data, historical monitoring data, and the data that caused the alarm and (5) continuous real time data as it is collected after the alarm. The EXD 20 may use a charger 52 to charge a rechargeable power supply 46 in the EXD 20.

Figure 2:
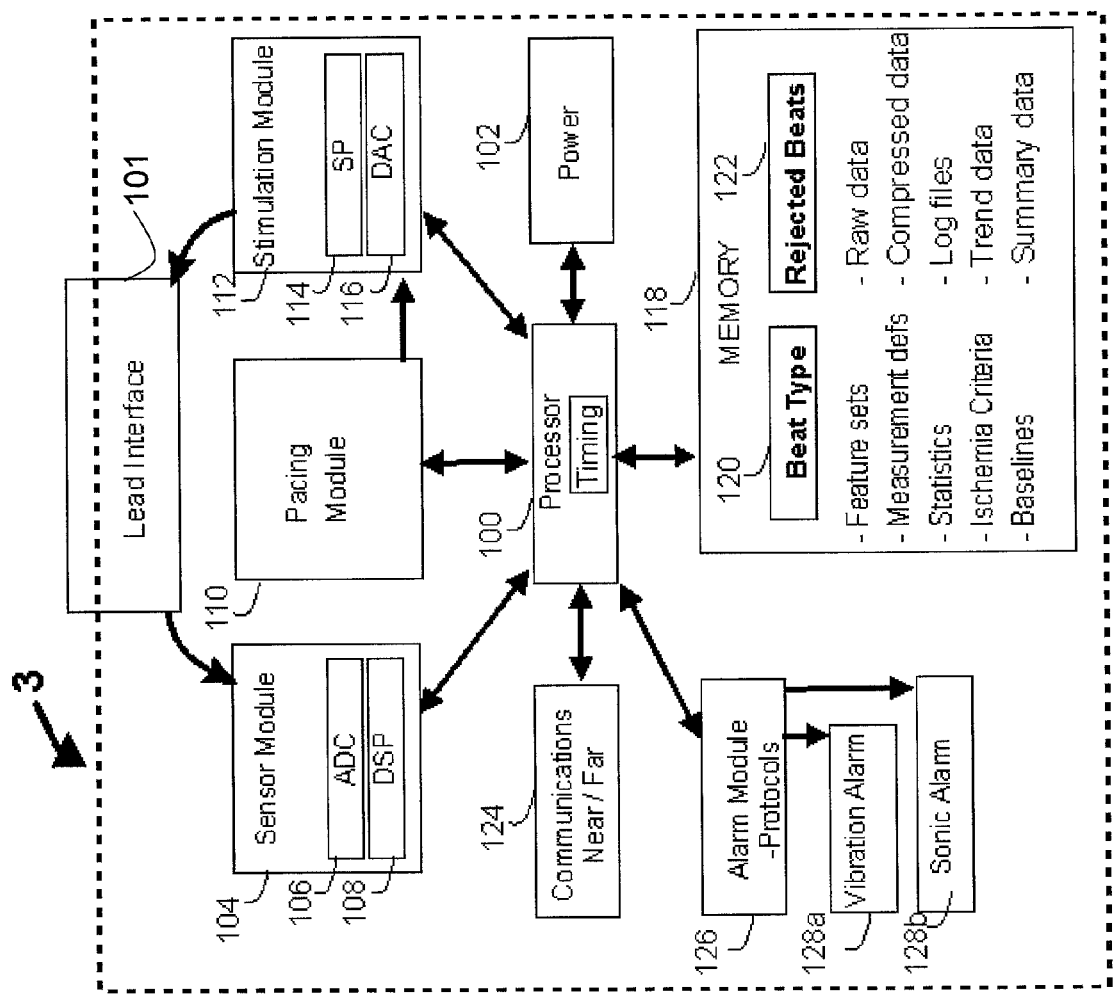
FIG. 2 shows a schematic of the functional modules of a device configured for monitoring ischemia in a patient who may sometimes have left bundle branch block

FIG. 2 is a block diagram of an embodiment of the IMD 3 shown in FIG. 1. The IMD 3 includes a processor 100 which is powered by a power module 102, having a power supply 102 that is for example a rechargeable lithium battery. The power supply 102 may include measurement circuitry for identifying power use or predicting battery end of life, and a means for receiving inductive charging if a rechargeable battery is used. The processor 100 is functionally coupled to the other modules of the IMD 3, such that communication and power are provided and the modules operate to provide monitoring, patient alerting, and pacing therapy. The processor 100 operates a sensing subsystem which can include a sensor module 104 that received signals from the leads 1 and 2 connected to the IMD 3 through the lead interface 101. Sensed data can be amplified and conditioned by the analog-to-digital (ADC) circuitry 106 and may be further conditioned by means of optional digital-signal-processing (DSP) circuitry 108. Alternately the processor 100 may receive and process the digital signals from the ADC 106. The sensor module 104 can also provide power (if needed) to any sensor which is used by the IMD 3. The processor 100 can process the sensed data from the ADC 106 or after pre-processing by the DSP 108 to measure selected features such as the amplitude or duration of cardiac data features (e.g. R-wave height and width, average ST-segment voltage and duration). Thus the processor 100 computes the value of one or more heart signal parameters based on the measurements of these selected features of the sensed signals.

The processor 100 and/or the sensor module 104 can communicate the sensed data to the pacing module 110 which analyzes the sensed cardiac data in order to determine if pacing is required and if so, then will also determine the type of pacing. These types of pacing include any combination of fixed or variable rate pacing, single or dual chamber pacing, anti-tachycardia pacing, defibrillation and cardiac resynchronization therapy. If pacing is required then the pacing module 110 can issue a command to the stimulation module 112 to provide pacing therapy through the leads 1 or 2 connected to the lead interface 101 of the IMD 3. The stimulation signal can be created by a signal-processing (SP) circuitry 114 which may include an arbitrary function generator and can then be converted to and analog signal and amplified by the digital-to-analog (DAC) circuitry 116. The processor 100 can use the memory 118 to store, for example, raw waveforms, measured features, summary data, computed statistics, measurement definitions, ischemia criteria, and an event logs. An event log can contain characteristics of the events and times of events that are registered by the processor 100 of the IMD 3. Events may include information such as the detection of ischemic beats, communications between the IMD 3 and EXD 20, delivery of pacing, patient notification, and any other event relevant to IMD 3 operation. The memory 118 may be accessed by the processor in a manner that allows it to function as a query-capable database. The memory module 118 can contain a beat type module 120 which is the parameterized description of LBBB and normal sinus beats used by the processor 100 to identify beat data as coming from a LBBB or normal sinus beat. The beat type module 120 may also allow the processor 100 to flag/classify any data which has been stored in memory as relating to LBBB or normal beat types. Further, datasets of stored sensed data for different beat types can include all data types (e.g., raw data, trend data, statistics) and can be calculated and operated upon separately by the processor module 100 under the guidance of the beat-type module 120. The reference data stored in memory 118 can include, as a function of beat type, ischemia detection thresholds related to size or duration criteria (or both), trend summaries of features, statistical calculations such as mean and variance. Alternatively, the reference data, log files, and other data stored in memory 118 may concatenate at least a portion of the data values across more than one beat type.

The rejected beats module 122 stores raw sensed/digitized data and statistics related to the description of rejected beats. Rejected beats can be classified into several categories. One type of rejected beat that the rejected beats module 122 tracks are either LBBB or normal sinus beats which are rejected from analysis, especially if these occur while waiting for a selected type of beat which is required to measure ischemia. For example, if the ischemia monitoring protocol attempts to measure normal sinus beats in order to measure ischemia and either LBBB or normal sinus beats have occurred, a running count of these beats is maintained by the rejected beats module 122. The processor module 100 may perform certain operations when selected rejected beat values exceed a selected level. Additionally, the module 122 can keep track of data that has been rejected due to noise or quality issues and can send notification if beats are rejected over an extended duration. Both the beat type and rejected modules will typically contain detection criterion associated with different types of beats. For example, PVCs may be identified by a shortened R-R interval and LBBB beats might be identified by an elongated QRS width associated with a QRS shape that is typical of the particular type of LBBB beat in question.

If the processor 100 analyzes the sensed data records stored in memory 118 and determines that a medical event has occurred which has been defined as requiring patient notification, it then operates to provide such notification and may do so in a manner defined by the alarm module 126 for the particular event. This may include operating the communication module 124 to attempt to communicate with external devices. The communication module 124 permits 2-way communication between the IMD and external devices and is configured for both near field communication (e.g. magnetic induction through the skin) and far field communication (e.g. the FCC medical band using the Zarlink chipset). In the case of an alarm that has been defined to have a vibration component, the vibration alarm module 128a having a drive circuit that powers a vibration motor (e.g. the vibrator motor used in a cell phone) to cause movement can be activated to provide a vibration signal as defined in the alarm module 126. Sonic alarms can also be provided by the sonic alarm module 128b that drives a sonic transducer such as a piezoelectric speaker to produce a signal that can be audibly heard outside the patient's chest. It is envisioned that patients would be alerted for a wide range of types of events including medically relevant events and device performance related events. Medical monitoring events trigger alarms when the processor 100 detects a medical event in the sensed data. For example, episodes of acute ischemia that may be indicative of a heart attack based upon a measurement of ST-shift which exceeds a specified threshold for a specified amount of time. For acute ischemia detection it is envisioned that the detection criteria including duration and thresholds would be different for when measured upon LBBB beats, normal sinus beats, or a mixture of the two. Alerting for device performance can also occur for events such as low power, failure to detect beats for a specified period of time indicative of lead or internal device failure.

The IMD 3 can analyze the cardiac data that is sensed by the implanted sensors 4,5 in order to distinguish between LBBB beats, normal sinus beats, transition beats and beats rejected for their failure to meet one or more acceptance criteria. LBBB beats can be identified according to features common for LBBB beats (e.g., a relatively longer QRS width and a known QRS shape), as will be further described with respect to FIGS. 15, 16a and 16b. Ventricularly paced beats, as measured by an electrode in the RV apex, often appear similar to LBBB beats. To distinguish between the two, a paced beat template is stored. Beats that have a general paced/LBBB morphology are characterized by a longer QRS than normal sinus beats, different QRS morphology than normal sinus beats and inverted T wave. Beats with the paced/LBBB morphology are distinguished from one another by applying template matching algorithms known in the art (and examining any pacing artifact, if present).

Further, distinguishing between sinus and LBBB beats can be accomplished by the analysis of the cardiac data in which LBBB beats are defined as having features that deviate from normal sinus beats according to beat type criteria which may be based upon prior data collected for that patient. Prior data of a patient can be used to adjust the beat-type criteria for improved classification performance. The device may detect ischemia, or ischemic data segments in segment-based approaches, by performing calculations on the number of detected ischemic beats which occurred within selected intervals. Further LBBB beats may also be excluded as candidate ischemic beats. In other words, some assessment strategies, LBBB beats may be counted as normal beats but not ischemic beats. For example, if under one ischemia detection algorithm, at least 25 of 40 beats must be identified as ischemic for medically relevant ischemia to be detected (i.e. over 50% of the last 40 beats must have been ischemic), and 20 beats have been detected as non-ischemic from normal sinus beats, while 20 beats were LBBB beats, then these other beat types may be used to satisfy the requirement for 40 total beats. Accordingly, beats of a particular beat type may be excluded from some types of analysis (not allowed to count towards ischemic beat count) and may be included in others (allowed to count for non-ischemic beat count). The IMD's processor module 100 is configured to analyze the sensed data from the leads 1 and 2 of FIG. 1 in order to accomplish a number of objectives. One objective of analyzing the cardiac data is to ensure that the data is of sufficient quality that it can then be used to detect ischemia.

Figure 3:
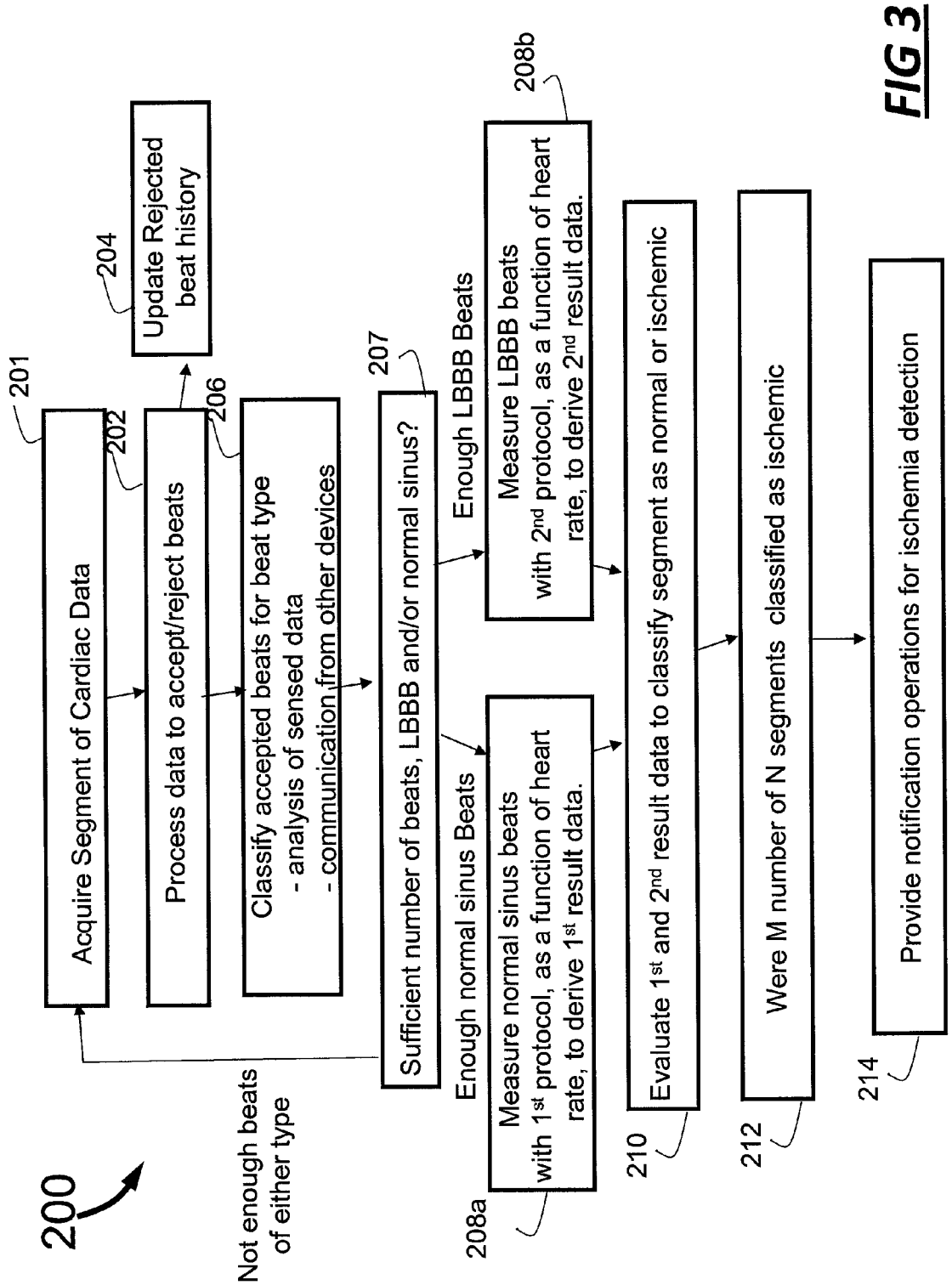
FIG. 3 shows a method for measuring ischemic related features of both LBBB and normal sinus beats in order to detect ischemia using a segment based detection scheme.

In FIG. 3, a process 200 for detecting ischemia using both LBBB and normal sinus beats is shown. In step 201 a segment of data is acquired and stored in memory 118 of the IMD 3 of FIG. 2. Data analysis using descriptions in the rejected beat module 122 of the memory 118 can allow the processor 100 in step 202 to accept or reject beats to be used in the subsequent analysis of ischemia. For example, beats which are too noisy, irregular, or partial beats which are the first or the last beat in a particular interval of cardiac data may be excluded from analysis, as may fusion beats if the IMD is also a pacemaker or used with a pacemaker. One method for detected irregular beats will be described with reference to FIG. 15. Data related to these rejected beats (e.g., for example whether these were LBBB or normal sinus beats corrupted by noise or an entirely different beat type such as a right bundle branch block beat or a ventricular beat) may be stored in the rejected beats module 122 in step 204 which can then be used to adapt the description of rejected beats for future use. Data portions which occur adjacent to axis shifts, or which also have electrical or other artifact that serves to decrease the quality of the recorded sensed data, may also be rejected. One example, of a quality check is to look for the $2^{nd}$ derivative of certain frequency range, wherein if this is above a specified level, then the data will not meet an acceptance criterion. Beats which are accepted can then be categorized by the processor 100 into different beat types (e.g. LBBB vs normal sinus beats) in step 206 using the descriptions stored in the beat type module 120 of FIG. 3. LBBB beats can be detected using a number of beat type criteria such as requiring the LBBB beats occur at a particular heart rate (e.g. the R-R interval is within a defined range). LBBB beats may require further criteria are met, such as requiring that LBBB beat contain a particular feature (such as a relatively long QRS interval compared to normal sinus beats which have been identified).

In one embodiment beats are measured and evaluated for ischemia in relation to beat type. Beats are classified as either ischemic or non-ischemic in steps 208a and 208b based upon a first ischemia detection criterion that is applied to normal sinus beats in step 208a and a second ischemia detection criterion that is applied to LBBB beats in step 208b. Applying an ischemia detection criterion to a given beat can comprise measuring a beat using a measurement protocol defined for that beat type and then comparing the measured feature to the respective ischemia criterion, which may be adjusted as a function of heart-rate for the sample of data being evaluated.

Next in step 210 of the process 200 the combination of identified ischemic LBBB and normal sinus beats from steps 208a and 208b are analyzed to see if there are a sufficient number of ischemic beats in a preset period of time to classify the segment or segments analyzed as ischemic. For example if 6 out of 8 analyzed beats either LBBB or normal sinus were classified as ischemic beats by steps 208a or 208b then the segment is classified as ischemic. It is also envisioned that if there can be separate detections based on LBBB beats or normal sinus beats with the decision to classify the segment as ischemic dependent on a combined detection criteria. For example if 5 out of 7 normal sinus beats are ischemic and no LBBB beats are ischemic, the segment might be still declared ischemic based on a normal sinus alone criteria even though 6 out of 8 total beats are not ischemic. Similarly if 2 out of 4 normal sinus beats and 2 out of 4 LBBB beats are ischemic, there might be a detection of ischemia due to seeing it in both paced types at a lower level that needed for detection for a single type or the two types together.

Alternatively, in a different embodiment after beats have been categorized as LBBB or normal sinus and then further characterized as ischemic or not, the average of the actual ST shift of all pertinent beats in a segment (rather than the number of detected ischemic beats which occurred within an interval of cardiac data) is used to categorize the segment of cardiac data which was collected. Additionally, characteristics such as the rate or size of changes of measured features may be used to classify the segments and detect ischemia. Segment based classification schemes in the detection of ischemia have been described in U.S. Pat. No. 7,558,623. As an alternative to segment based detection of medically relevant ischemic events, calculations can be performed upon detected LBBB and normal sinus beats which occurred within an interval of cardiac data, where LBBB beat acceptance criteria and normal sinus beat acceptance criteria can be used to determine how large a change must be in order for a beat of a particular beat type to be included in a running sum which is used to detect a medically relevant ischemic event (see, the Rate of Change Applications mentioned in the Summary of the Invention). In these cases, either individual beats or segment averages may be used to provide detection of ischemic events worthy of patient notification.

In the next step 212 a recent history of segments are evaluated in relation to ischemia event detection. An ischemic event is different than classifying beats or segments as ischemic and its detection is the trigger for specific actions such as the initiation of patient alerting or wireless data transmission to the remote monitoring center 22 of FIGS. 1 and 2. Ischemic events occur when more than a specified number of segments are classified as ischemic, for example, 3 adjacent ischemic segments may be required for detection of an ischemic event. In response to the detection of ischemia notification by step 214 of the process 200 may occur through the alarm module 126 of the IMD 3 of FIG. 3 or using the wireless communication module 124 of the IMD 3 which can be configured to communicate with an external patient device, patient programmer, or other type of external device such as a third party device which is located in a hospital. Additionally, such wireless communication as provided by modules 26, 36, 124 can provide notification of ischemia to a remote party such as the patient's doctor or the remote monitoring center 22. This may occur directly, such as the internal device communicating with a cellular or wide area network (WAN), or via the external pager type device which then relays this communication. The monitoring device can contain alerting means for providing notification when ischemic events are detected. If the patient is to be alerted then there may be transducers to allow this to occur such as vibrators or sonic transducers. Additionally, alert signals and data, or simply data, may be sent to a remote party according to a protocol when data has been identified as having ischemic beats that have the potential to be medically relevant and which should be reviewed prior to alerting the patient. There are many types of medical notification strategies. Some of these are automatic and notify the patient directly, others send data to a remote station where it is automatically or semi-automatically processed in order to determine if a patient is experiencing a medically relevant event requiring notification/intervention. All of these known methods may be used with the current invention.

Rather than combining two different beat types, the processor 100 of the IMD 3 can be further configured to classify a segment or measure ischemia by only counting ischemic beats of one beat type when a sufficient number of such paced or normal sinus beats exist within a specified interval, while rejecting the others from analysis. For example, if in step 202 it is found that 8 out of 11 beats of a cardiac data sample are normal sinus beats, then instead of attempting to incorporate the paced beat in to the analysis of ischemia, the LBBB beats can simply be rejected and excluded from further analysis, aside from updating the rejected beat history in step 204 with this information. In the case where there are not enough normal sinus beats in a segment in step 207, rather than incorporating the LBBB beat information, the processor 100 can also be configured to increase the duration of data collection by a selected amount (by returning to step 201) in order to attempt to collect more normal sinus beats (also see FIG. 8). Further, this attempt may be repeated more than once. Alternatively, a minimum delay such as 90 seconds may be introduced between these subsequent attempts.

Figure 4A:
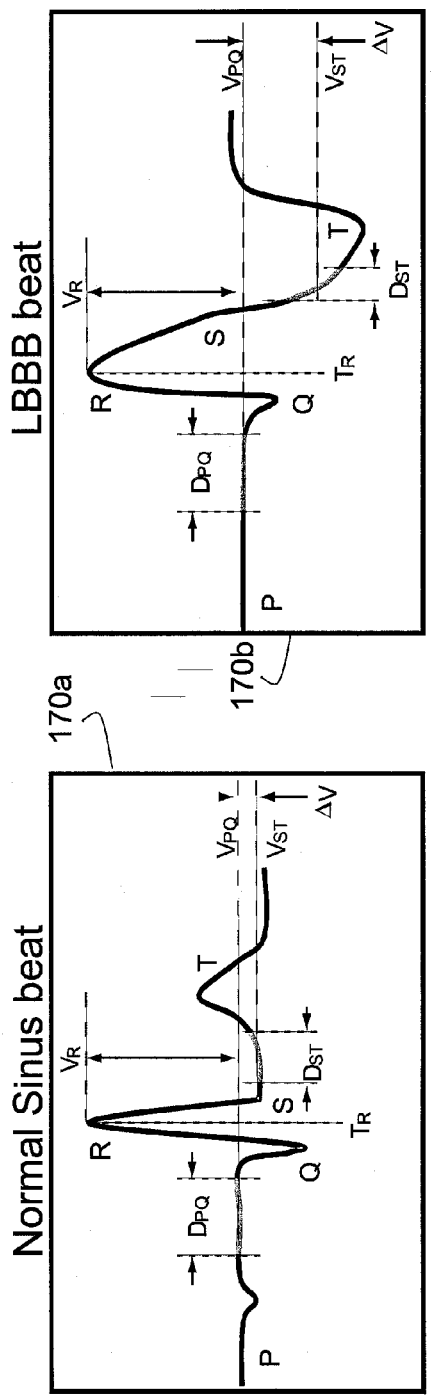
FIG. 4A shows two columns of figures for LBBB and normal sinus beat types, respectively, with sample cardiac features measured in the two types of beats.

The analysis of cardiac data by the processor 100 includes measuring features of each beat type. FIG. 4A illustrates features which may be measured for normal sinus and LBBB beats in the first and second column, respectively, from a can-to-tip perspective. For FIGS. 4A and 4B the LBBB beats which are shown are representative of an individual with chronic ischemia. In the case of the normal sinus beat a clear QRS complex is shown, which allows measurement of the R-wave height, while in the case of a LBBB beat the QRS complex demonstrates an expanded width. The same features may be measured for different beat types, and this may occur using identical definitions of beginning and end latencies or identical intervals but with different start times. For example, in for both LBBB and normal sinus beats the R-wave may be measured based upon the largest slope alternation within a candidate heartbeat, while in the ST segment may have the same duration but a delayed start time for LBBB beats which have a widened QRS. Alternatively, different features may be measured for different beat types, where the LBBB beat may not include the same measured features as those derived for the normal sinus beats. The features that are defined differently for each beat type include interval definitions (e.g. start times and durations) during which the defined features must occur in order to be included in the evaluation of ischemia. Accordingly, the measured features of each heartbeat can be defined differently for each beat type so that features are measured using a normal sinus measuring protocol to measure normal sinus beats and an LBBB beat measuring protocol to measure LBBB beats.

Figure 4B:
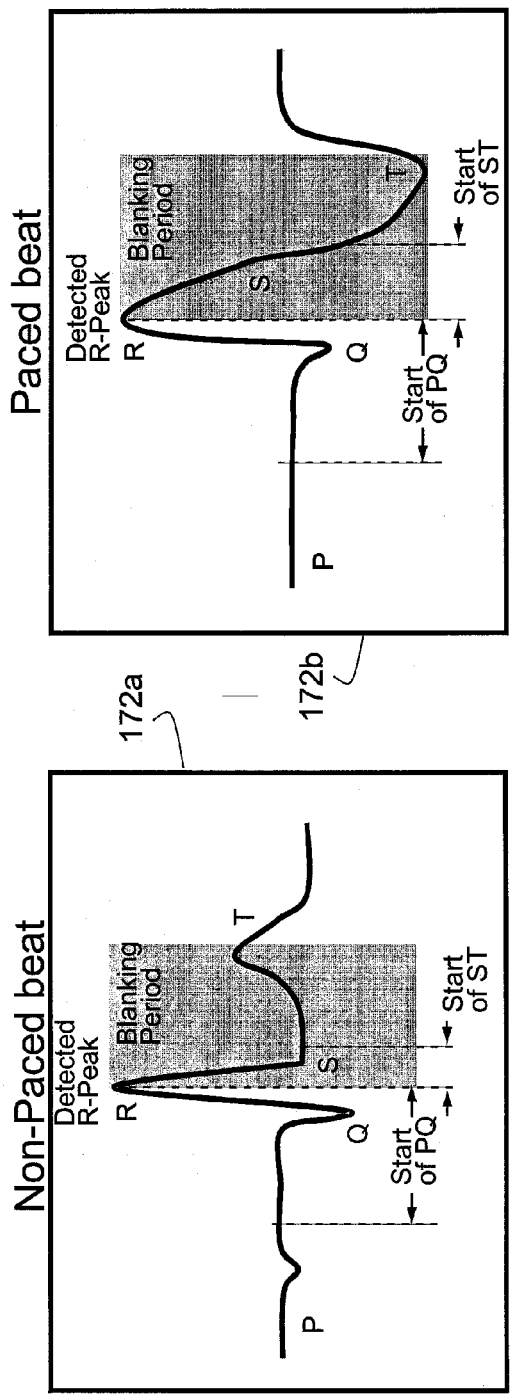
FIG. 4B shows two columns of figures for LBBB and normal sinus beat types, respectively, with sample protocol parameters which are used to measure heart-beat features in the two types of beats, such as defining blanking intervals.

The rules used to define acceptable activity which is measured in each type of beat may also vary as a function of beat type. The FIG. 4B shows a "blanking period" which is used to define a period during which a subsequent R-wave may not be measured subsequent to an R-wave which has just been detected. This period is useful, for example, in preventing algorithms from identifying waveforms incorrectly such as may occur when a T-wave is incorrectly identified as an R-wave. These examples illustrate features of the different measurement protocols that could be used in steps 208a and 208b.

In an alternative embodiment, ST deviation is measured with respect to ST and PQ points that are found based on methods described in U.S. patent application Ser. No. 12/721, 836, filed Mar. 11, 2010, assigned to the assignee hereof, entitled "QRS ONSET AND OFFSET DETECTION WITH ADAPTIVE TEMPORAL WINDOWING," which is incorporated by reference herein.

Figure 4C:
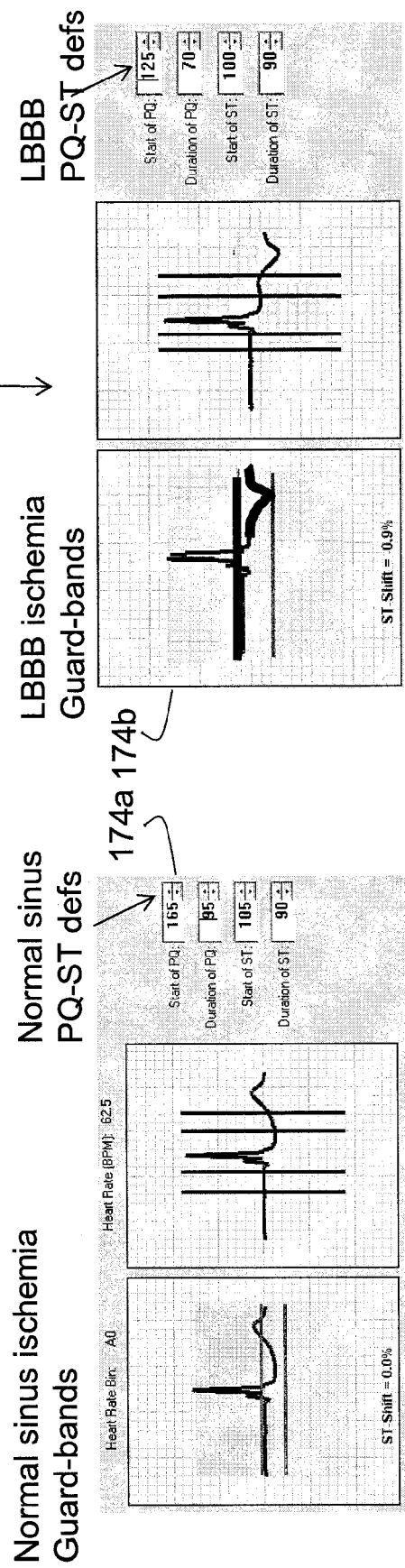
FIG. 4C shows two columns of figures for LBBB and normal sinus beat types, respectively, with examples of how graphical interfaces can be used to set parameter values for measuring features and evaluating those features in relation to ischemic criteria.

Once the processor 100 has measured the relevant features of each beat type and calculated the values of specific heart signal parameters for the beat type, these are operated upon to detect ischemia. One manner of processing compares the value of one or more heart signal parameters for a beat type to a first and a second ischemia detection criterion, for normal sinus and LBBB beat types respectively. In this manner, when the two types of criteria, which may be heart-rate dependent, are applied to a measure which includes the ST-segment, as measured from either of the two types of beats, then each beat can be classified as ischemic or not. FIG. 4C, shows a graphical user interface for viewing/setting the upper and lower ischemia detection thresholds. On the left the ischemia thresholds for normal sinus beats are shown as lines above and below the heart beat. Also shown are intervals in which the PQ and ST segments are allowed to be detected, with graphical controls for setting latencies relative to the identified R-wave peak of each beat. On the right side of the figure, similar information is shown as defined for the LBBB beats.

The ischemia detection thresholds shown in FIG. 4C, may be based on the difference between ST segment and PQ segment voltage defined here as "ST-deviation". Features, such as ST-deviation, may not be compared directly to a criterion, but rather to previously measured features. For example, the difference between the ST-deviations of the beats of the current set of data and an appropriate reference (e.g. a reference calculated for a particular beat type) can be evaluated. When a baseline reference value is compared to a current ST-segment value, a measure of ST shift can be calculated and the equation used to evaluate each beat may be:

$$ST\text{-Shift }\%_{type} = ((PQ\text{-}ST_{base}) - (PQ\text{-}ST_{type}))/RPQ_{type} * 100$$

Where $ST\text{-Shift }\%_{type}$ is the normalized difference between the current ST-deviation and a baseline ST-deviation average value for a particular beat type. Normalization may be made using the R-wave reference height to the PQ segment from a collection of baseline beats with references set separately for LBBB and normal sinus beat types (i.e., $RPQ_{type}$), or simply using a baseline R-wave reference value which is used for both beat types. In this latter case, a correction coefficient may be used. For example, R-wave height for normal sinus beats may be multiplied against the correction factor before being used to calculate the ST–shift % for the LBBB beats. It may be preferred however to use a single value for amplitude normalization but allow different thresholds for ischemia detection for LBBB vs normal sinus beats. It is also envisioned that any baseline signal amplitude measurement such as QRS height can be used here for normalization.

Figure 5:
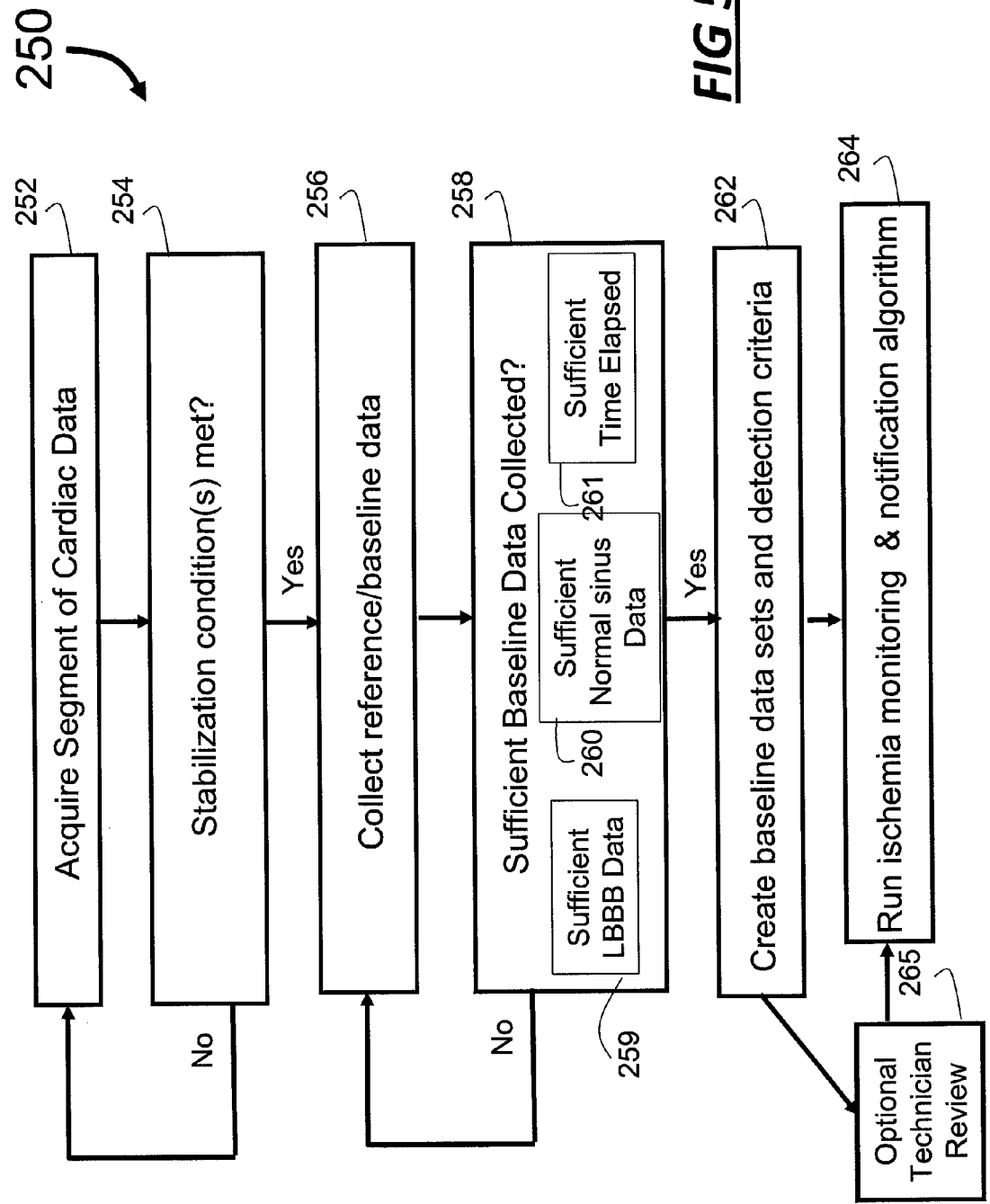
FIG. 5 shows a method for creating two different types of baselines which can serve as a self-normative reference for LBBB and normal sinus beats.

As an alternative to classifying beats as either normal or ischemic, and performing calculations on this binary set of results, one can quantitatively assess cardiac features and the changes which occur in the beats over time and in relation to reference values. Further, rates of change as a function of time may be used to derive important features in the data. In one embodiment, time rate of change measures are calculated separately for each beat type and ischemia is detected separately for each beat type in the manner described in the Rate of Change Applications mentioned in the Summary of the Invention In one embodiment of the present invention, self-normative or "baseline" data is used by the IMD 3 as a reference to which currently sensed data is compared. FIG. 5 shows an example of the process 252 by which the IMD 3 of FIG. 1 would initiate collection of such baseline data. Once the IMD 3 is implanted it would be programmed to begin acquiring cardiac data; however, obtaining reference data does not begin until a stabilization condition has been met in step 254. This is to ensure that following surgery, the characteristics of the electrode-tissue interface have stabilized and that factors such as injury current are not biasing the shape of heart-beat features. An example of such a stabilization is that of implanted electrodes, where there is a one to 7 day time period during which injury current from the implantation affects the signal typically creating a significant ST voltage offsets. It is also envisioned that the stabilization condition of step 254 could be a time delay, e.g. 7 days.

Once the stabilization condition(s) in step 254 is(are) met, the IMD 3 would begin collecting baseline data from the implanted sensors in step 256. Step 256 will also include the ability to reject beats that fit rejected beat descriptions as stored in the rejected beat module 122 of the memory 118 of FIG. 2.

In step 258 the IMD 3 will determine if sufficient baseline data has been collected to calculate a baseline data set in step 262 and initiate cardiac monitoring. The step 258 may include processes 259 which determines if there is a sufficient amount of LBBB baseline data collected, process 260 that determines if there is a sufficient amount of normal sinus data collected and process 261 that determines enough time has elapsed to that the data is representative of a sufficient period of time. Once this time condition is met the step 258 could then run processes 259 and 260 to determine if sufficient numbers of LBBB and normal sinus data has been collected and then move on from there.

Since the IMD 3 is designed to detect ischemia on both LBBB and normal sinus beats, there are several ways in which the steps 256 through 264 can be implemented.

In one embodiment, both LBBB and normal sinus beat baseline data is collected in step 256 and the IMD 3 will have sufficient baseline data collected when there are either enough paced or normal sinus beats analyzed by step 258. For example, if in step 258 at a given time there are enough paced baseline beats but not enough normal sinus beats, the IMD 3 will go to step 262 and create a baseline and detection criteria for LBBB beats and begin cardiac ischemia monitoring for LBBB beats only while an ongoing baseline creation process which is part of step 264 continues to update the paced beat baseline and tries to collect enough normal sinus beats to create a normal sinus baseline and detection criteria and begin ischemia monitoring on normal sinus beats in step 264. This embodiment could act in a similar manner if there are enough normal sinus beats but not enough LBBB beats in step 258 by allowing cardiac monitoring to begin after there is sufficient normal sinus baseline data collected.

In all of the baseline data calculations the acceptance of normal sinus beats may be limited to "normal" beats meeting one or more criteria such as that the R-R interval for the beat lies within a specified "normal" range.

It is also envisioned that step 262 could be performed by the physician's programmer 18 of FIG. 1 which has been sent baseline data from the IMD 3. The programmer 18 may function in an automatic mode with automatic return of detection criteria back to the IMD 3, in a manual mode where the operator of the programmer 18 uses the programmer to calculate and or set detection criteria and then return them to the IMD 3 or in a semi-automated mode where the programmer calculates the detection criteria but the operator checks the result before it is downloaded back to the IMD. The manual or semi-automated modes can also be done through data communication with the remote monitoring center 22 in step 265 where a technician can either calculate and return detection criteria to the IMD 3 or the technician can verify and accept the calculation from step 262 and enable implementation and initiation of step 264. Step 264 also includes patient alerting appropriate to the type of ischemia detected.

The stabilization condition of step 254 can also, for example, require that the net change of a feature is above or below a selected level, a rate of change of one or more cardiac features (e.g., as evidenced by trend data) is below some level, or some feature measured in the data is present or absent (e.g., fluctuation of noise level is within a specified range defined for stability which may indicate that a subcutaneous lead has interfaced sufficiently with surrounding tissue). Additionally, when pacing is provided, stability can be defined based upon a consistency of a cardiac feature that is measured after pacing is delivered. For instance, the threshold needed to achieve pacing decreases in the initial period after implantation. Pacemakers can automatically adjust for this using auto-capture feature which adjusts applied energy as a function of physiological threshold. The auto-capture feature may be used to determine when enough time has elapsed since implantation so that baseline data collection can be initiated. Additionally, the assessment beats which are used to determine when baseline collection can be initiated may be designed so that only LBBB or normal sinus beats are used. For example, evaluating both LBBB and normal sinus beats, without consideration of beat type may produce sensed cardiac data which does not reliably reflect the actual injury current well. Since R-wave and ST-segments may look different for sinus and LBBB beats, it can be difficult to assess changes in beat features over time when more than one beat-type is considered.

The ischemia detection criterion produced by step 262 can be based upon statistical measures that are calculated for the upper and lower boundaries of the normal range of a patient based upon the baseline data. The upper and lower thresholds can be calculated independently rather than simply being a measure such as mean+/−3 standard deviations. Further, the detection criterion can be based upon non-parametric or parametric statistics computed upon the reference baseline data and may be calculated using probably distributions of this data (e.g., bootstrapped confidence limits). The detection criterion can also be set in relation to the most extreme values found in a patient during a reference period. Multiple criteria can be used that can be heart-rate dependent and specific to a particular beat type.

Figure 6:
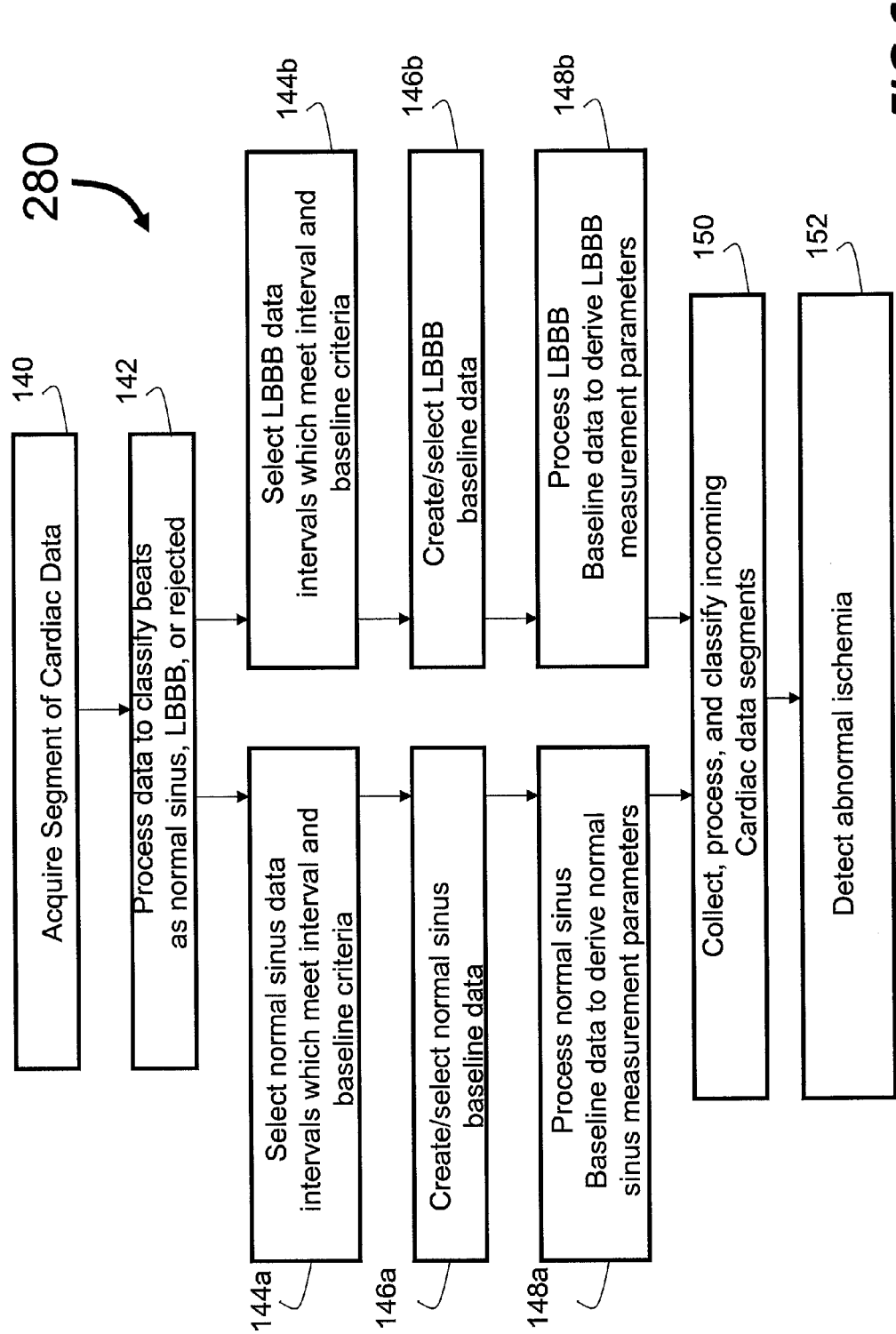
FIG. 6 shows a method for ischemia monitoring which includes obtaining baselines and measuring features in both LBBB and normal sinus beats for baseline reference data, and then collecting, processing, and comparing the measured features of current data for each beat type to their corresponding baselines in order to classify cardiac data and detect abnormal ischemia.

Several types of baseline data can be obtained. For instance, baseline data can be obtained for each of two or more beat types. FIG. 6 shows another embodiment of the present invention method in which baseline data are collected for LBBB and normal sinus beats. In step 140 cardiac data are sensed according to an ischemia monitoring protocol. In step 142, the sensed data are processed in order to classify normal sinus or LBBB beats. The data may be analyzed in order to determine if particular beats can be classified as either of the defined beat types and to then make their associated measurements.

After the beats are classified as LBBB or normal sinus, the next step is to select beats that meet both "interval criteria" and "baseline criteria" 144a, 144b. Interval criteria can entail requiring sensed data in the interval to meet noise-criteria, or can require that the interval be characterized by having at least a selected number of recognized beats. Baseline criteria can require that a selected number of beats in the interval are either LBBB or normal sinus. Another type of baseline criterion can require that the beat data be constrained to cardiac data having beats-per-minute values which are within a specified range such as the normal resting range of an individual. This can be termed "resting heart rate range baseline criteria". Next in steps 146a and 146b, appropriate baseline data from prior data collection and processing is selected or created for use in steps 148a and 148b. Additionally, more than one set of baseline data can be obtained whereby baselines for different heart rate ranges are stored to serve as reference data for when currently sensed data correspond to the same range. In step 148a the normal sinus baseline data are used to derive "normal sinus measurement parameters" such as a reference value which contains statistical measures such as the mean and variance of ST-deviation, averaged R-wave height, or other parameters for a selected portion of baseline data which have been collected. The same is done for the LBBB beats 148b. These statistical measures can be used to determine ischemia thresholds used during subsequent monitoring. Additionally, the baseline data can be analyzed by the IMD3 or by medically trained personnel in order to create the definitions for how beats will be measured as is shown graphically in FIG. 4C, where a graphical user interface allows the start and duration values to be defined which will then be used to measure subsequent data. In step 150, the ischemia monitoring occurs and includes collecting, processing, and classifying incoming cardiac data according to the ischemia monitoring protocol. The incoming data can be defined within segments which can be classified in various manners (e.g., as ischemic or not) or can be evaluated in relation to individual beats, but preferentially a segment based protocol is relied upon. Step 150 can also include using sensed data to create a recent baseline dataset which may span the current data and a prior period such as a 4, 8, 12, or 24 hour period. The recent baseline data can be used to create a recent reference dataset against which new data will be compared in order to determine if there has been a medically relevant change in the ischemic status of the patient. In step 152, the results are used to detect abnormal ischemia which is medically relevant to the patient and this will lead to ischemia detection operations such as alerting the patient or sending data to a remote party.

The detection of medically relevant ischemic events may be defined differently as a function of beat types that are resident within the cardiac data that have been measured. In the case of segment-based analysis of ischemia, normally 3 segments are required to be abnormal prior to ischemia being detected. In the case of paced-beats, this number may change. In other words the criteria for detection of ischemic events that trigger alerting of a patient may change as a function of beat type. Further, if the segments contain mostly LBBB beats (e.g., 80%) then the criteria can be different than if few beats (e.g., 20%) are LBBB. In the same way, while segments of data may require 3 normal sinus beats (out of 8 or so) to be ischemic before the segment is classified as ischemic, a different number (e.g., 4) of LBBB beats may be required in order to classify the segment in that manner. In one aspect, when beats of both types are used, these may be treated as identical and the total number of ischemic beats is simply counted across the specific interval or for a specified number of beats.

In one embodiment, reference data is collected during an initial period of about 1 week. During this time the patient may undergo an optional stress test in order to ensure that beats are collected over a wider range of heart rates. This reference data can be collected and can be classified into LBBB and normal sinus interval which can then be used to set ischemia criteria. For example, the difference between the PQ segment voltages and ST-segment voltages may be used to calculate a measure termed ST-deviation for both LBBB and normal sinus beats. ST-deviation, or additional measures, may then be evaluated to obtain statistical measures, such as the mean and standard deviation of the ST-deviation measure, which can be used to set ischemia thresholds. As cardiac monitoring progresses the newly collected baselines may be used as reference data to update the ischemia detection criteria and related statistics which are used to evaluate current cardiac data. Initial reference data which are collected are not only used to set ischemia detection thresholds, but can also be used to determine how beats of a particular beat type are measured. The detection of the start and stop latencies of a feature such as ST-segment can be accomplished either automatically, by the device, or under the guidance of a medical professional using a graphical user interface such as that shown in FIG. 4C. Further, once measurement parameters that will be used to measure one type of beat are set, these may be used to set the measurement parameters that are used for measuring features of a different beat type. For example, the ST-segment end latency for LBBB beats can be set to be 10% longer than that which is set for the normal sinus beats. Parameters used to measure features of LBBB beats may be prorated according to measures defined for normal sinus beats of the patient.

Steps 140 to 148 can occur prior to the beginning of monitoring and then can occur periodically during monitoring in order to update a dataset of recent baselines to which incoming data is compared. Each of the baseline datasets can require a minimum number of recent collected beats to be present in order for to the baseline data to be used. These beats can be used to create running averages or sums, may be used to compute mean and standard deviations for various measures, or may be otherwise combined. In a preferred embodiment at least one sample (segment) of beats is collected every hour for each of 24 hours so that each baseline is calculated upon 24 datasets, or statistical summaries of these sets. Alternatively, baseline data may be collected across 6 different intervals, each spanning 4 hours, or 4 different intervals each spanning 6 hours, in each 24 hour period. It is a preference to use at least 4 sets of data in any average in order to maintain the stability of statistical measure computed upon the baseline data. When possible, the baseline data should be collected between the prior 1 hour and the prior 48 hours, in relation to the current data being assessed so that it is not too old. Data which is older than 48 hours can be considered "stale" and my not serve well as a reference to which current data should be compared because the patient's state may have changed since the baseline data were collected. Further, baseline datasets may be required to have a minimum number of beats in order to be considered reliable, such as 100 beats, and these beats may be required to be less than 4 days old.

Since the detection of ischemia is based on an analysis of a particular beat type with its respective baseline, detection can only occur if adequate baseline data exists for that type. In the case where baseline data is not available for a particular beat type then several alternatives include: alert the patient to see their doctor; increase the sampling time of data segments that are sensed; decrease the time between when data segments are sensed; reject a selected beat type from the analysis; use an absolute or relative value criterion; use the baseline data (such as particular parameter values and threshold criteria) for a beat type that is different than the current beat being evaluated (i.e. use the baseline for normal sinus beats to evaluate LBBB beats), and further this baseline data can be multiplied by a correction factor to be appropriately used in the evaluation of a different beat type).

Alternative ischemia detection algorithms which do not rely upon a baseline reference may also be used. These may be used in addition to baseline-based ischemia detection protocols, or alternatively, when a baseline is not available or is not available for a particular beat type. As mentioned above and as will be further described below, one ischemia detection strategy is to look at the time-rate of change of at least one heart signal parameter and to detect ischemia when the cumulative change over a short period exceeds a criterion.

Rather than use of within beat-type reference data, the measured features of a particular beat type can be compared to data obtained for a different beat type. For example, a LBBB beat can be compared to a normal sinus beat reference value. Data from LBBB beats which have different timings relative to the normal sinus beat may be compared in the detection of ischemia.

Figure 7:
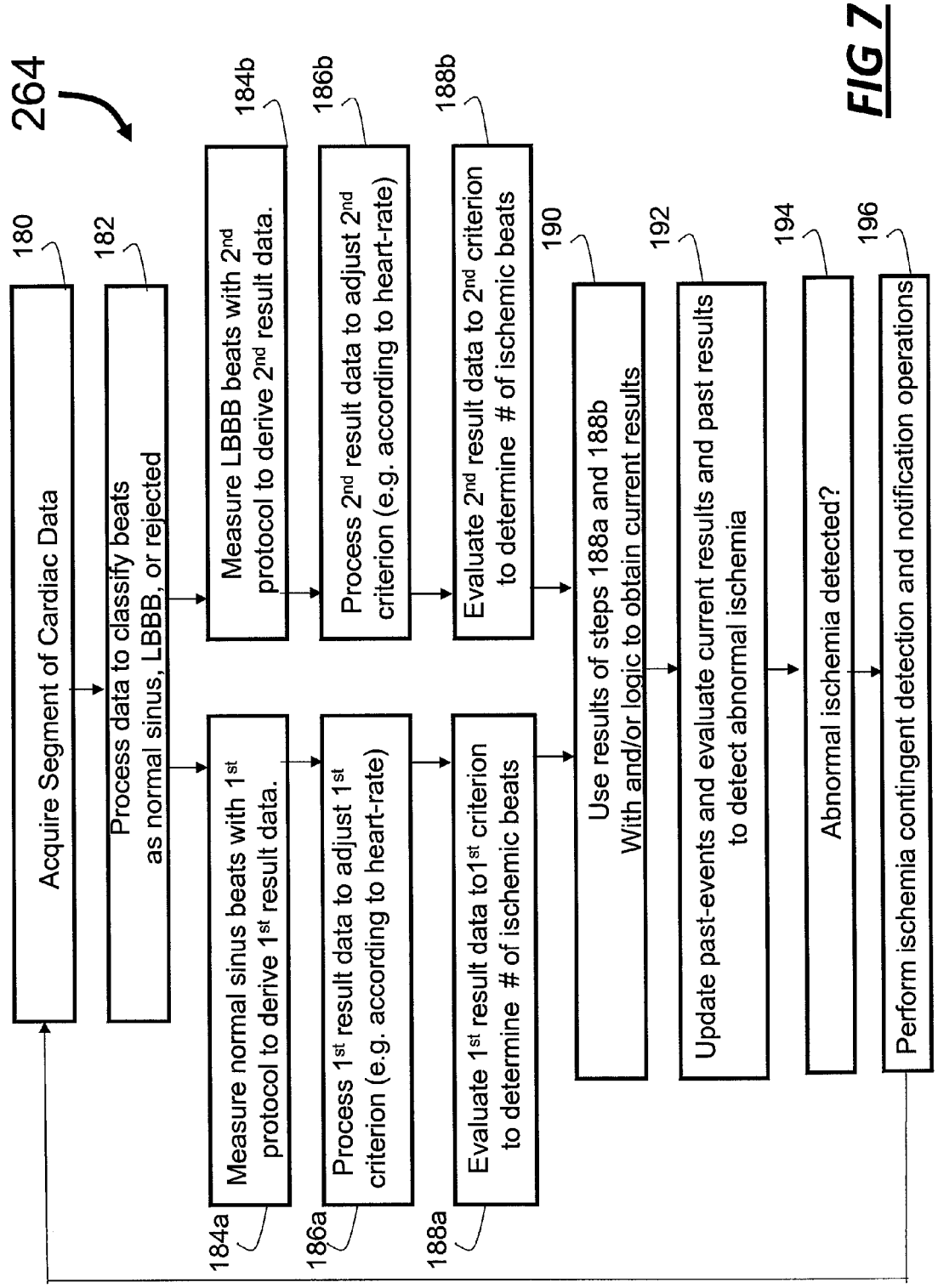
FIG. 7 shows a method for ischemia monitoring which includes monitoring LBBB and normal sinus beats separately and combining the monitoring of the two beat types in the detection of ischemia.

FIG. 7 shows one embodiment of step 264 of FIG. 6 which is includes a method for detecting ischemia during daily life monitoring. Step 150 of FIG. 6 could be realized as steps 180 to 182 here. In steps 180 the ischemia monitoring protocol determines that the acquisition of a current data set is warranted. In step 182 the beat waveforms of the sensed cardiac data (and other data if this is also sensed by other sensors) are classified into normal sinus or LBBB beats or are further analyzed for arrhythmias or otherwise rejected. The processor 100 of FIGS. 1 and 2 is configured to assess data for each beat type only after applying data acceptance criteria to the cardiac data and rejecting data that does not meet the data acceptance criteria from being evaluated further. In the case of data that will be used for baseline data, then these criteria are called baseline data acceptance criteria. Acceptance criteria may vary as a function of beat type. For example, data acceptance criteria can also be used to ensure that fused beats are not evaluated as paced-beats by rejecting these from the analysis.

In step 184A the features of the normal sinus beats are measured using a first protocol to derive a first set of result data. In step 186*a*, the first set of result data are used to adjust a first criterion which is used to evaluate the data. For example, the average heart rate of the first set of result data is calculated and is used to select the ischemia detection criterion that will be used to evaluate the heart beats of the first data set. In step 188*a* the heartbeats of the first result data are compared to a first criterion in order to determine the number of ischemic beats. This step can include computing the ST segment voltage/ST-deviation for each beat and comparing that to the ST segment voltage/ST-deviation reference computed upon the normal sinus baseline data, and then comparing the calculated differences to an ischemia criterion at the appropriate heart-rate which was calculated from the variance of a reference dataset of normal sinus baseline data. In steps 188*b*, 186*b*, and 188*b*, the method is repeated using data from paced-beats. Alternatively, based upon the ischemia monitoring protocol selected, the baseline data that is available, or the prevalence of normal sinus and LBBB beats in the recent history of sensed data available in the reference data, only steps 184*a*-188*a* or 184*b*-188*b* can be provided. In step 190 the results of steps 188*a* and 188*b* are combined in order to obtain current results. In step 192 the recent history of past results is updated (for example, the prior "current results" are moved further down a FIFO array that may be part of the memory 118 is used to hold the result data) and then the current results and past results are evaluated in order to provide ischemia detection. For example, if the current results and the 2 most recent sets of past results are all classified as ischemic rather than normal, then a medically relevant ischemic event will be detected. In the case where ischemia is detected 194, then the defined ischemia detection and notification operations occur 196, whereas if no ischemia is detected then the method reverts back to step 180.

The IMD 3 of FIG. 1 can be set to apply separate ischemia detection criteria for the data of each beat type of LBBB and normal sinus beats. The ischemia detection criteria that are used to detect ischemic beats may require that an ST-segment measure (e.g., ST segment voltage, ST-deviation, ST-shift, or ST–shift %) remain within a particular heart-rate related range (that can vary as a function of beat type), and may require further conditions be met such as requiring that changes (e.g. increases) in this measure occur at a particular rate, within a particular time-frame, or remain within a particular range of size. Ischemic beats can be detected using detection criteria which compare at least one heart signal parameter of current data to the patient's self-norm data and determine, for example, if this comparison exceeds a pre-set detection threshold for a particular beat type. The detection threshold may be calculated based upon either patient self-norm data, or population-matched data, with respect to a particular beat type. Relative changes (comparing features of current data to those of reference data) or absolute levels (of features in the current data) may be assessed by detection criteria, and further a combination of both these approaches may be used for either beat type.

In another aspect, an IMD 3 for monitoring ischemia and providing pacing in an ambulatory patient has a sensor implanted to sense cardiac data from a patient's heart and a processor 100 which is configured both to distinguish between LBBB and normal sinus beats and to reject beats that do not meet acceptance criteria. The processor 100 analyzes the collected data and, in conjunction with information from the pacing protocol, detects beat samples for each beat type across a number of defined sensing periods. The processor 100 is also configured to access data from a non-electrical sensor such as an accelerometer and to use this non-cardiac data in order to adjust the analysis of cardiac data, for example, by adjusting the ischemia thresholds used to detect ischemic status of heartbeats. The processor 100 is further configured to measure heart signal features both for current sensed data and for baseline reference data and to calculate at least one statistical measure upon these heart signal features for each beat type such as mean, sum or variance. The processor 100 may thus generate at least one statistical measure for each beat type and these measures can be used either to calculate criteria for ischemia detection (in the case of baseline reference data) or can be compared against these criteria (in the case of currently sensed data). The sensing periods for baselines can be defined to occur over a prior time period, e.g. 24-hours, and may also be contingently adjusted based upon trends which occur in the historical records of sensed data. Likewise, current data may be sensed in a discontinuous manner, for example, 10 seconds of data collected every 90 seconds, may be continuous, and/or may be event driven by characteristics detected in the data monitored. Prior baseline reference data from the patient, including normal heart rate range baselines can be termed patient self-norm data and may be segregated and operated upon as a function of beat-type. Patient self-norm data for a heart signal parameter can be compared to current heart signal parameter data and ischemia detection can be made by comparing current and self norm data against a pre-set detection threshold. This also may be specific to a particular type of beat (e.g. sinus or paced) and which is dynamically adjusted based upon recent cardiac activity.

Figure 8:
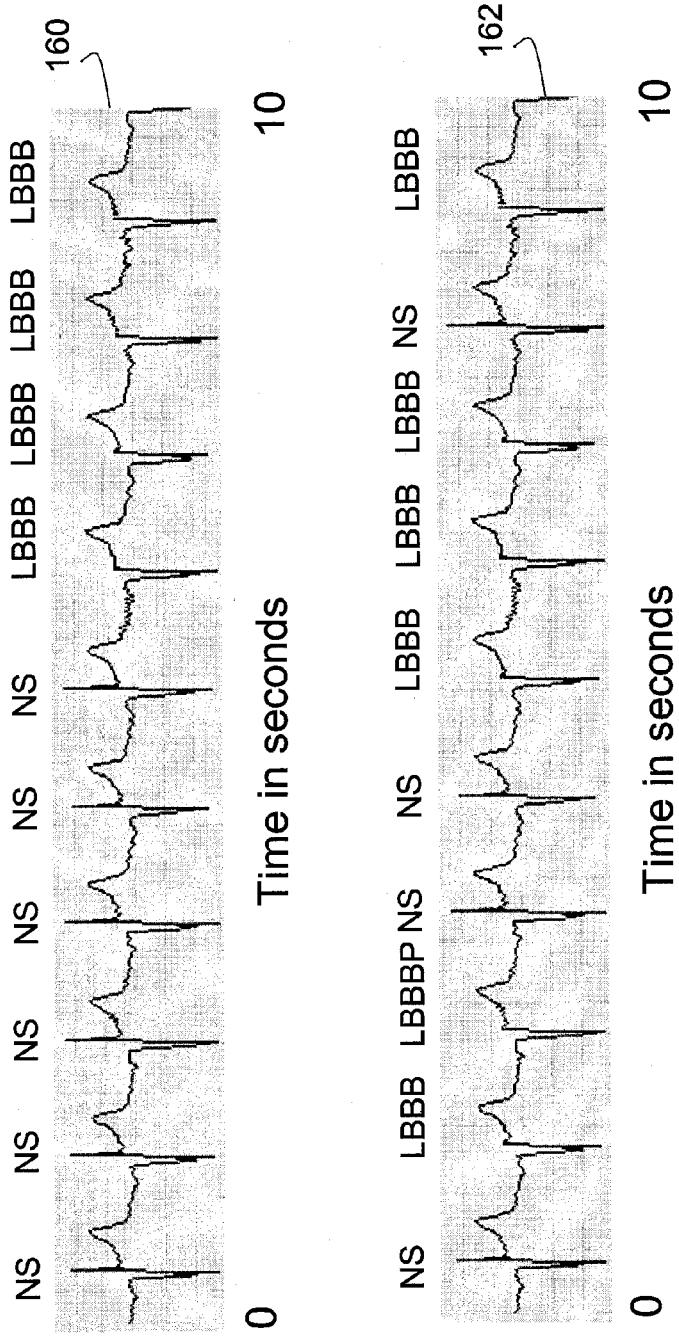
FIG. 8 shows a segment of cardiac data containing both normal sinus and LBBB beats and demonstrates one beat type difference that can be evident in the ST-segments of these different beat types.
Figure 10:
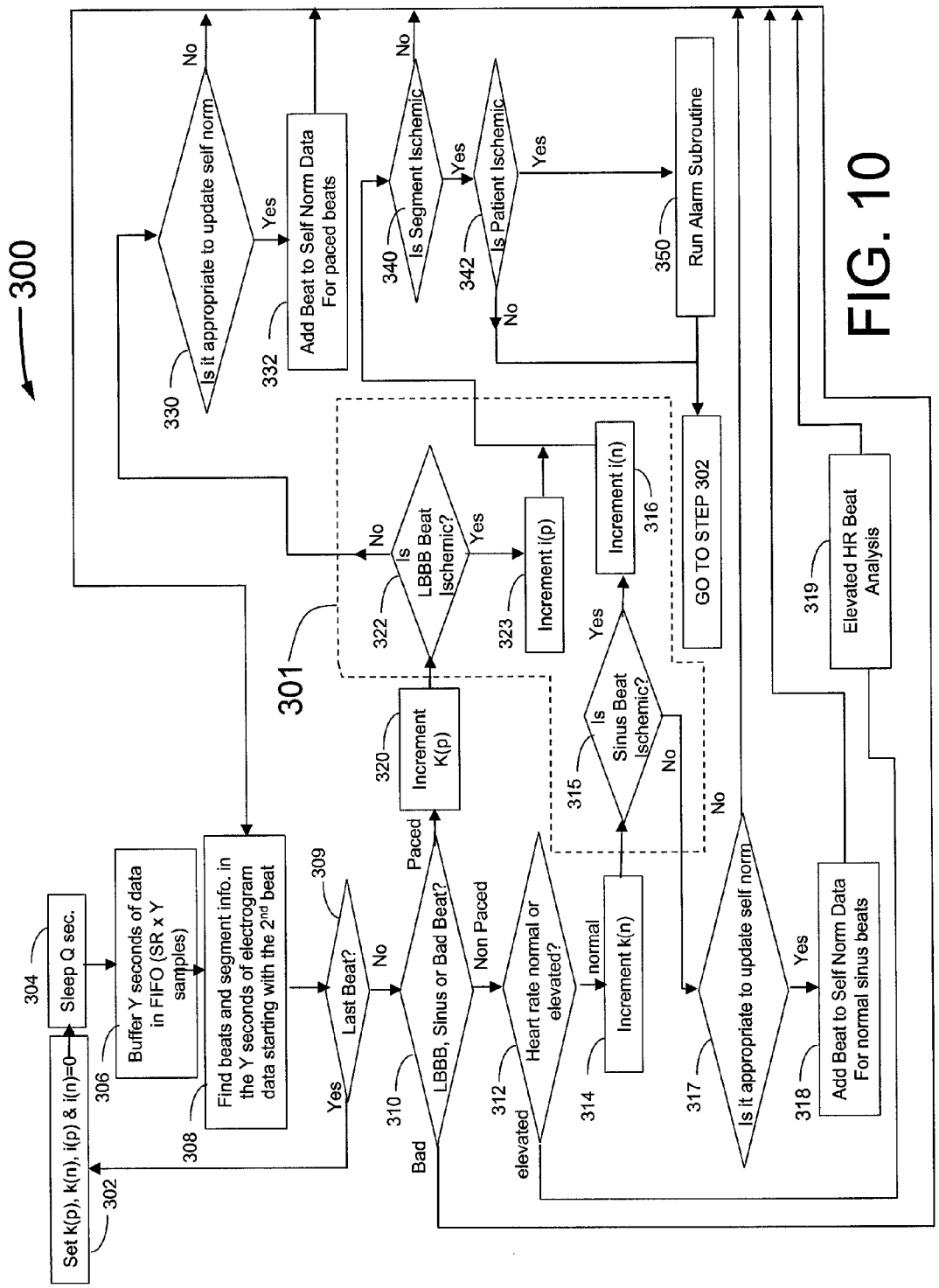
FIG. 10 shows steps of a method used to obtain self non-native data for both LBBB and normal sinus beats.

FIG. 8 shows two electrogram segments of 10 seconds each. The top electrogram segment 160 is characterized by 6 normal sinus beats followed by 4 LBBB beats. The LBBB beats of this figure are simulated and are provided for demonstration purposes, the morphology of actual LBBB beats will often deviate considerably from those shown. The first and tenth beats may be immediately excluded by the ischemia monitoring algorithm since the features of these beats may not land fully within the measured segment and the first segment has no prior beat with which to reference R-R interval. The remaining beats may each be measured using normal sinus and paced protocols, respectively, to obtain normal sinus and paced beat features. The normal sinus and paced beat features may then be compared to reference data for the two types of beats to derive quantitative results. The quantitative results for each beat type may be combined, or may be compared to ischemic thresholds for each beat type in order to obtain qualitative results such as non-ischemic or ischemic. The quantitative and/or qualitative results can then be used by an ischemia detection algorithm that evaluates individual beats or the entire segment in its detection of ischemia. In the lower segment 162 shown, LBBB beats and normal sinus beats are interspersed. Under certain protocols, this distribution may cause the segment to be rejected, or certain beats may be rejected (or may cause data collection to be extended as shown in the example of FIG. 10). The order of beats may be used in the analysis of the cardiac data. In one example, the manner of evaluating the beat may change depending upon whether the beat is the first paced beat or a subsequent beat. Likewise, the first normal sinus beat may be treated differently (e.g. rejected from analysis) than subsequent normal sinus beats.

There may be morphology changes in the heart beats occurring during the transition from paced to normal sinus and back. Thus one embodiment of the present invention would intentionally ignore (or otherwise treat differentially) any beat that is not preceded and followed by a beat of the same type thus negating any morphology changes in the transition from paced to normal sinus beats and back. For example in FIG. 9, if transition beats were to be avoided then the top and bottom electrogram segments would have the same number of acceptable LBBB beats (i.e. 3) since beat 7 would be rejected from the top electrogram segment and beats 1, 5 and 9 would be rejected as being transition beats.

Figure 9:
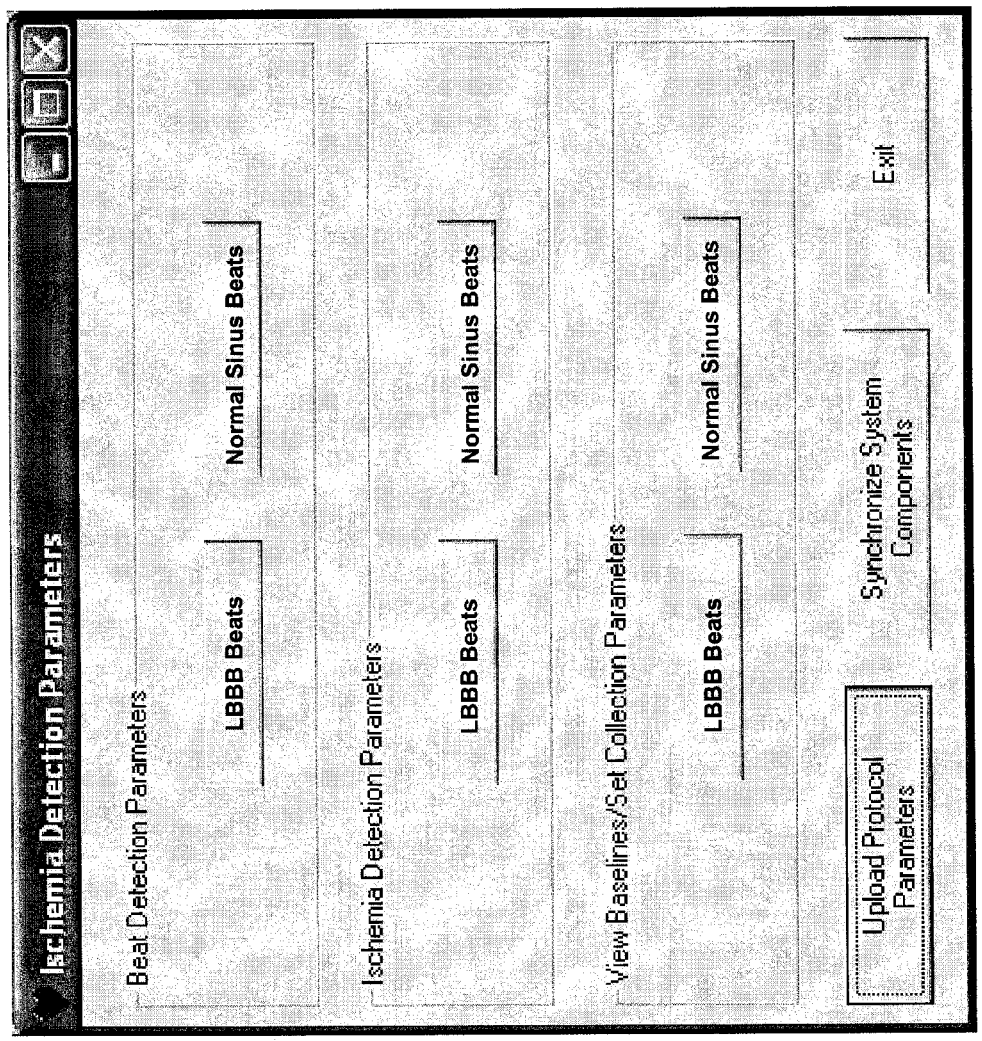
FIG. 9 shows a programming screen for adjusting beat measurement and ischemia detection characteristics used for both LBBB and normal sinus beats.

FIG. 9 shows a display screen of the programmer 18' of FIG. 2 for the IMD 3' which is related to setting parameters used to monitor ischemia in a patient that has LBBB beats. The "beat detection parameters" buttons allow the user to configure the IMD measurement protocols used to measure features of LBBB and normal sinus beat types (see FIG. 5A-C). The "ischemia detection parameters" buttons allow the user to configure the IMD ischemia detection protocols used to assess features of LBBB and normal sinus beat types and to determine if a beat is ischemic (see FIG. 5C). The "View baselines/set collection parameters" buttons allow the user to view baselines and summary statistics for baselines collected for each beat-type and to configure the IMD measurement protocols used to measure baseline data for LBBB and normal sinus beat types. Additionally, there an "upload" button which allows the programmer to directly upload this information by communicating with an implanted IMD 3 of FIG. 1, its EXD, or its programmer. The "synchronize system components" button allows the programmer to synchronize the values defined on this screen with the other system components. This can also occur automatically when exiting the screen or when terminating or establishing communication with the IMD 3'. The "Choose mode" field allows the medical practitioner to select one of 3 possible default or starting detection modes which are oriented towards different occurrences of left bundle branch block and are: Mode 1 (rare LBBB), mode 2 (continuous LBBB), mode 3 (mixed LBBB and normal sinus beats).

FIG. 10 diagrams an example of the main loop 300 of the process for detection of ischemia in patients with pacemakers. The process begins in step 302 by setting the counters k(p) (number of total LBBB beats), k(n)(number of total normal sinus beats), i(p)(number of total ischemic LBBB beats), i(n)(number of total ischemic normal sinus beats) to zero. The loop 300 then in step 304 waits Q seconds before step 306 that collects and stores in a First-In-First-Out (FIFIO) buffer Y seconds of data at a sampling rate of SR samples-per-second for a total of SR×Y samples. Both Q and Y may be either constant values or may vary depending on other steps of the process. For example, in one embodiment the main loop 300 would sleep Q=80 seconds then collect Y=10 seconds of data if the heart signal appears to be within the definition of normal but change to X=20 seconds and Y=15 seconds if abnormalities are detected. These abnormalities include ST segment voltage changes exceeding half the detection threshold for ischemia, too many short R-R intervals indicating PVCs or other arrhythmias or an interval that reflects a transition to a period when there is little or no pacing for a substantial period of time. The FIFO buffer is typically part of the memory 118 of FIG. 3.

Step 308 follows to identify each beat starting with the $2^{nd}$ beat of the Y seconds of data and sends the digital signal samples to step 309. Step 308 also sends segment information to step 309 such as the R-R interval for the beat as measured from the prior beat and whether the beat is the last beat in the Y seconds. In step 309 if the beat is the last beat then the loop 300 will return to step 302 to begin again. The first and last beats are typically excluded from analysis because the first beat has no known R-R interval from a prior beat and the last beat may have important features such as the ST segment or T wave missing. The loop 300 continues with step 310 if the beat is any beat but the first or last beat.

Figure 13:
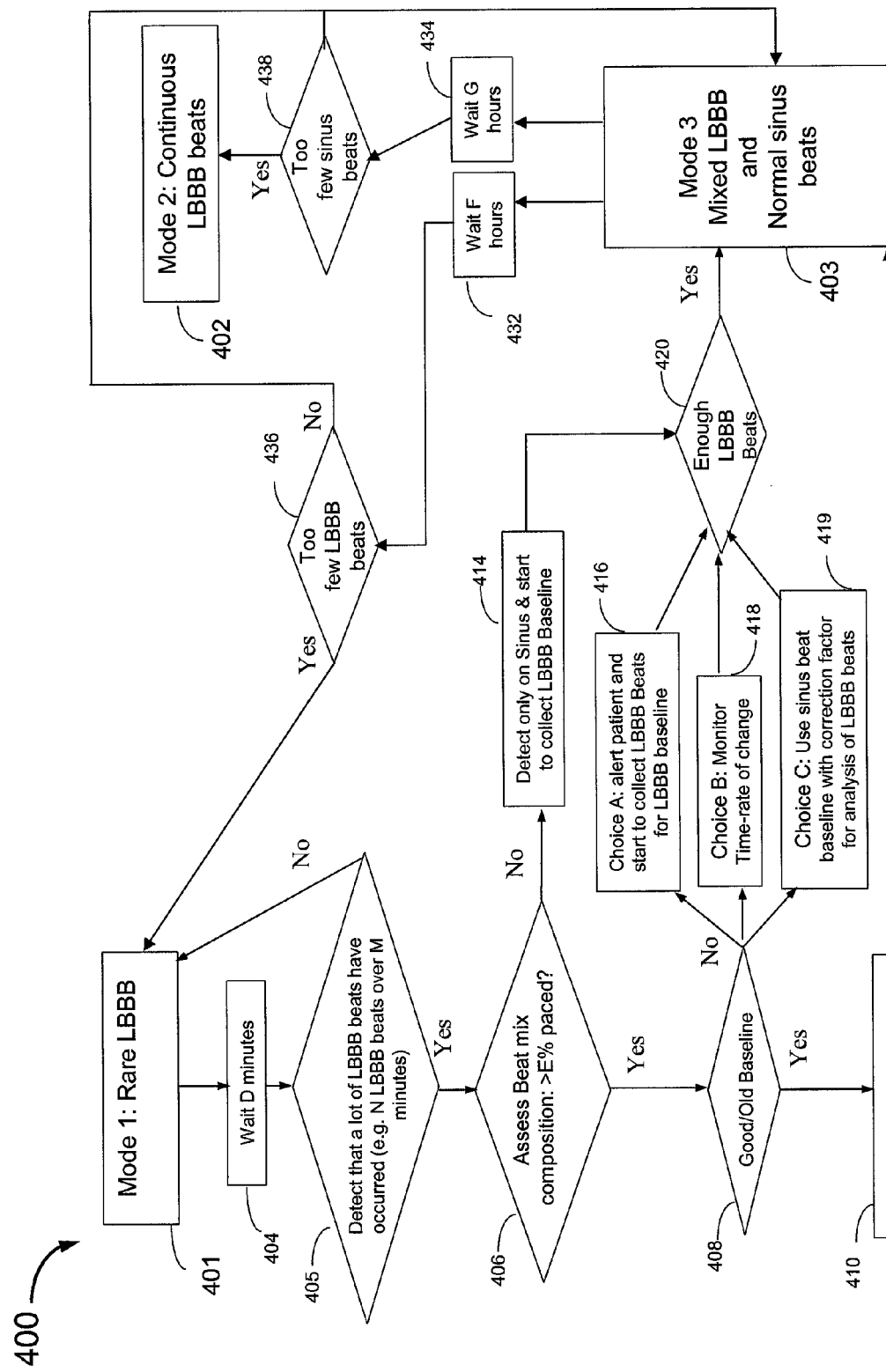
FIG. 13 shows steps of a method used to transition from Mode 1 in which LBBB beats occur rarely to Modes 2 or 3 when the pattern of LBBB beats changes for a patient.
Figure 14:
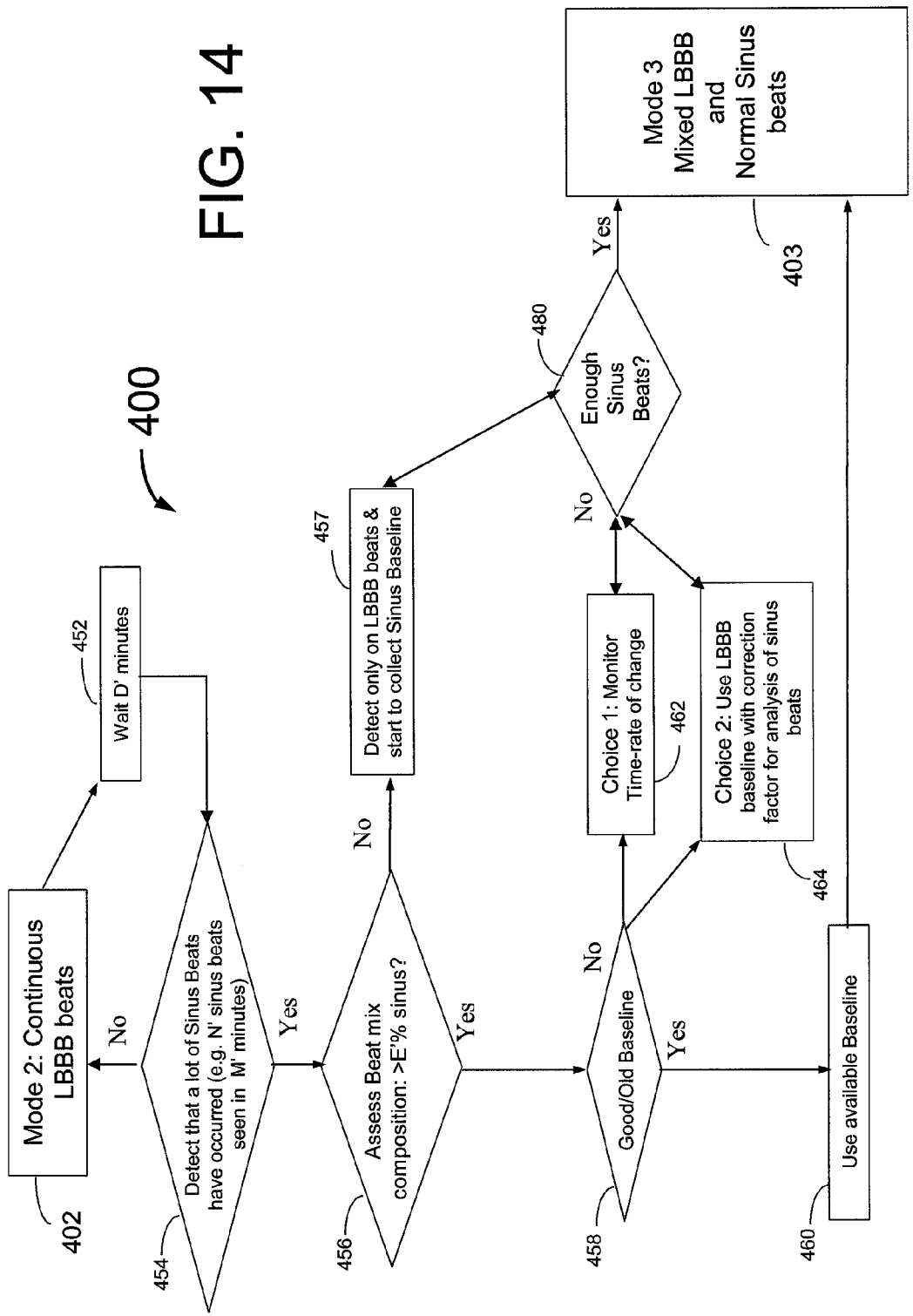
FIG. 14 shows steps of a method used to transition from Mode 2 in which LBBB beats occur frequently to Modes 1 or 3 when the pattern of LBBB beats changes for a patient.

Step 310 analyzes the digital samples of the beat and classifies the beat as paced, normal sinus or bad (rejected). For LBBB and normal sinus beats, step 312 checks which detection mode is operative. The operative detection mode is determined according to the method that will be described with reference to FIG. 13. In Mode 1, which corresponds to rare LBBB beats, LBBB beats are rejected unless choice C/block 419 in FIG. 13 is implemented. In Mode 2, which corresponds to very frequent LBBB beats, normal sinus beats are rejected unless choice 3/block 466 in FIG. 14 is implemented. In Mode 3, neither LBBB nor normal sinus beats are rejected. If in step 310 the beat is classified as "bad" or rejected, then the main loop will go back to step 308 and get the next beat.

If the beat is not of the LBBB type, step 312 will then check to see if the R-R interval for the beat is appropriate to the preset normal heart rate range for the patient. If it is elevated above the normal range, then the loop 300 goes to step 319 where it performs analysis on the beat at elevated heart rate. An example of such an analysis is shown in the Hi/Low Heart Rate subroutine in FIG. 9 of U.S. Pat. No. 6,669,023 by Fischell et al. If the beat is in the normal heart rate range, the loop 300 then goes to step 314 where it increments the count of normal sinus beats k(n) and then step 315 analyzes the normal sinus beat to see if it is ischemic. An example of step 315 is included in FIG. 11 which includes the steps 315, 316, 322 and 323. If the beat is ischemic then step 316 increments the counter of ischemic normal sinus beats i(n) and proceeds to step 340 to see if the Y second long segment is classified as ischemic. FIG. 12 shows an example of the steps 340 and 342. If the beat is not ischemic the main loop 300 then proceeds to step 317 where if it is appropriate to update the self norm/baseline data for normal sinus beats. The determination in step 317 of what is appropriate may be based on time criteria, for example if it has been at least one hour since the last time 8 beats were collected for analysis in determining self norm values. If it is appropriate, in step 318 the beat is analyzed and the measured heart signal parameters are used to update the self norm/baseline data for normal sinus beats in the manner described in U.S. patent application Ser. No. 12/367,155, entitled "Baseline Processing for the Detection of Cardiac Events", filed February 2009 and owned by the assignee hereof. If in step 317 it is not appropriate to update the self norm data or after the self norm data has been updated, the loop 300 returns to step 308 to get the next beat.

If in step 310 the beat is an LBBB beat, step 320 increments the count of LBBB beats k(p) and then step 322 analyzes the beat to see if it is ischemic. If it is ischemic then step 323 increments the counter of ischemic LBBB beats i(p) and proceeds to step 340 to see if the Y second long segment is classified as ischemic. If the beat is not ischemic the main loop 300 then proceeds to step 330 where if it is appropriate to update the self norm/baseline data for ischemia detection. Being appropriate may involve similar or different conditions than that used in step 317 for normal sinus beats. If it is appropriate, in step 332 the beat is analyzed and the measured heart signal parameters are used to update the self norm/baseline data for LBBB beats. If in step 330 it is not appropriate to update the self norm data or after the self norm data has been updated, the loop 300 returns to step 308 to get the next beat.

If in step 322 or step 315, a beat of either beat type is classified as ischemic, then step 340 will check to see if the Y second long segment can now be classified as ischemic. If it is not ischemic, then the loop 300 returns to step 308 to get the next beat. If the segment is ischemic, the main loop 300 goes to step 342 to see if the patient can be classified as ischemic. Such classification may include the cardiac features showing changes which are large enough to surpass ischemia detection criteria and can include evaluating the recent history of how segments have been classified to see if the ischemia has existed for longer than a selected duration. In the preferred embodiment, the patient is classified as ischemic if for example, three consecutive segments are classified as ischemic or 4 out of 7 consecutive segments are classified as ischemic. If in step 342 the patient is ischemic then the main loop 300 goes to run the alarm subroutine 350 which may also include the transmission of event and alarm information to external equipment and medical personnel. The alarm subroutine 350 may also include the capability to differentiate two types of ischemic conditions that occur at normal heart rates. The first of these are recovery events much like a failed stress test where the patient has an ischemic episode that follows a period of elevated heart rate. Recovery events usually indicate a stable form of ischemia that can be treated on a non-emergency basis, typically by implanting a stent at a narrowing in the patient's coronary artery. The second type of ischemic event which occurs without a prior period of elevated heart rate is much more serious and may be the indication of a heart attack. For this reason, these two types of ischemic events may trigger very different alarms. Recovery events may not even warrant an alarm, but may cause the storage of data for later physician review, initiate a minor alert to the patient to see their doctor soon, or may cause the data to be transmitted to a remote station 22. The second type of alarm however should be indicated as an emergency which alerts the patient to call 911 and get to a hospital as soon as possible because heart attacks can otherwise result in death or severe damage to the patient's heart.

Figure 11:
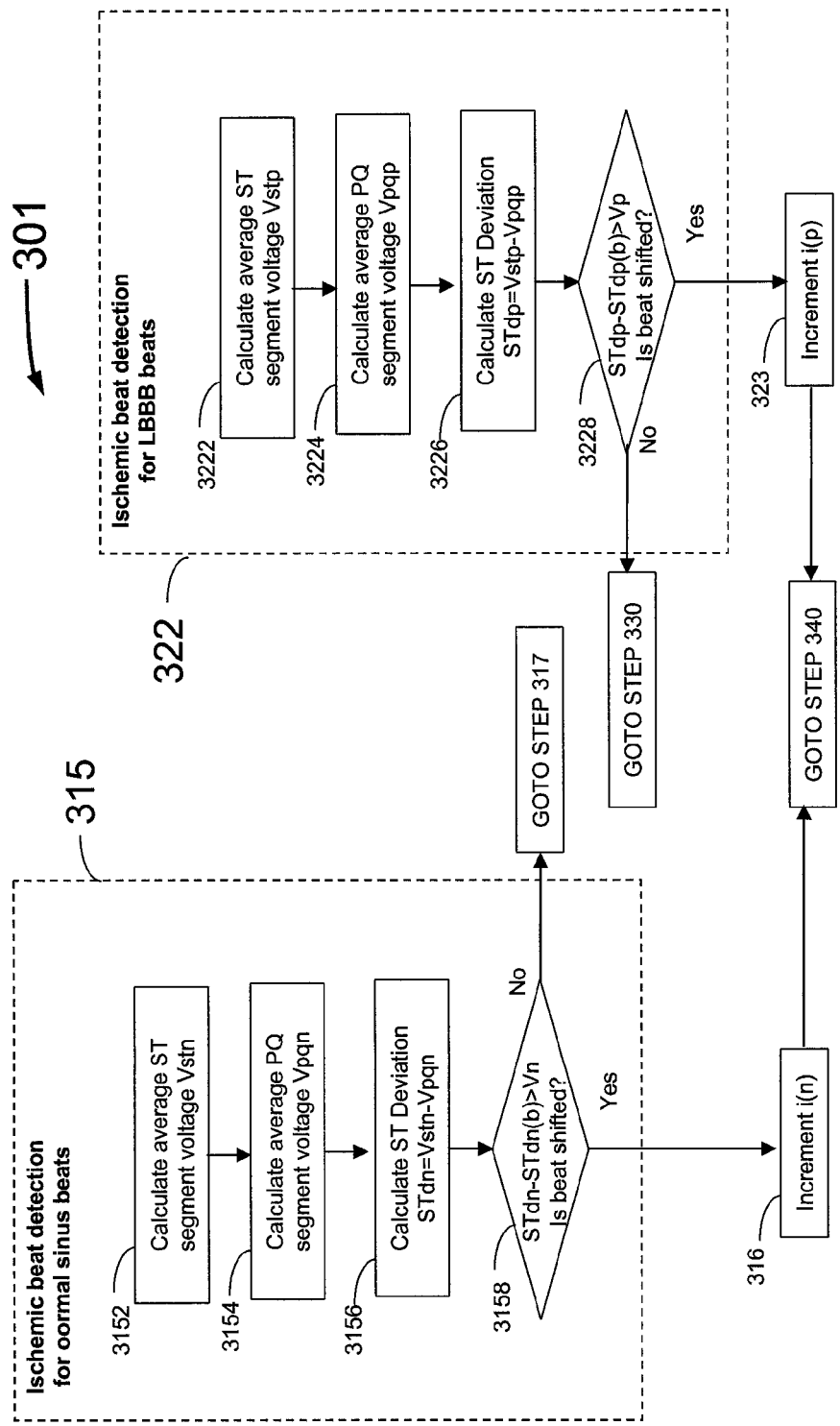
FIG. 11 shows steps of a method used to obtain self normative data for both LBBB and normal sinus beats.
Figure 12:
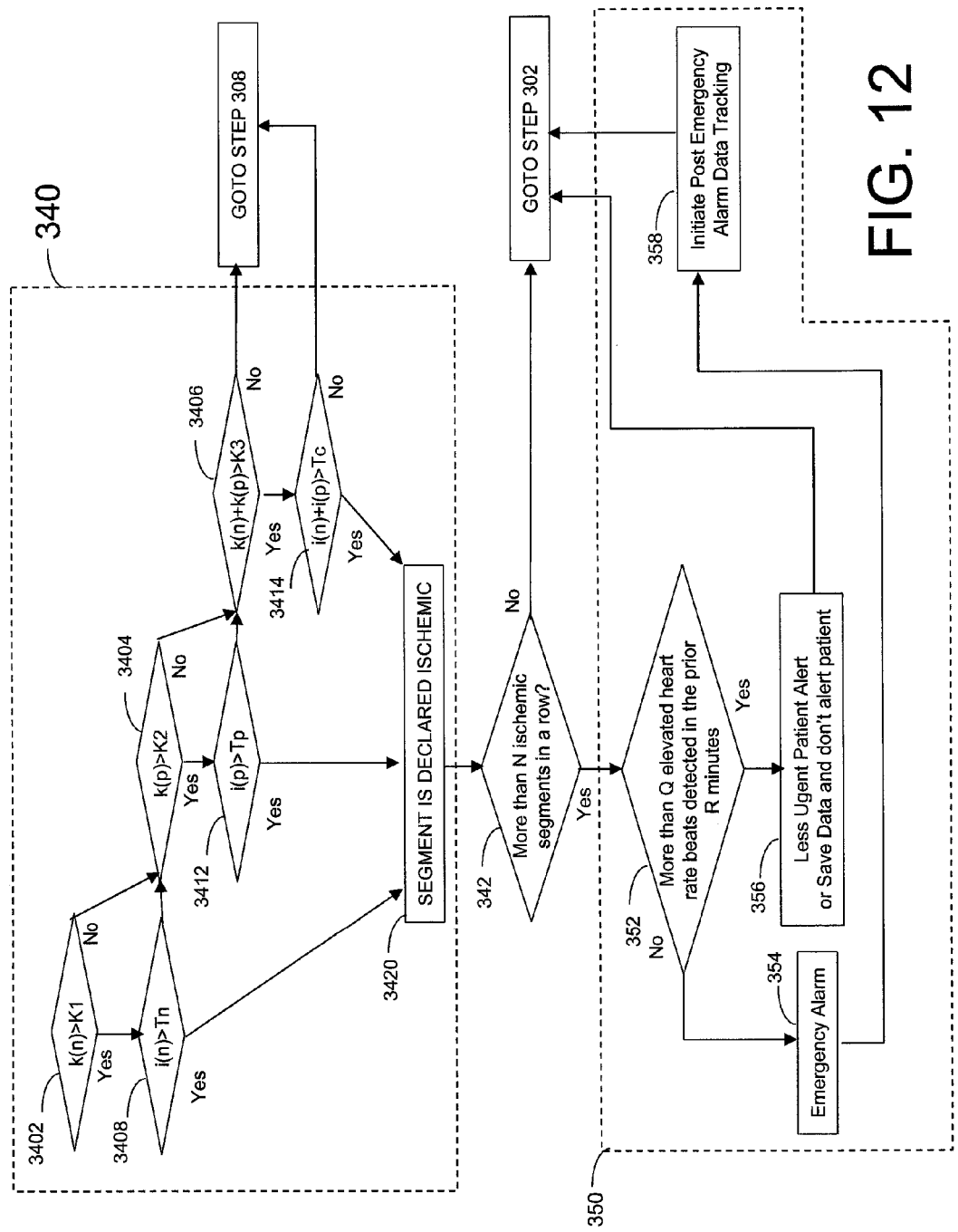
FIG. 12 shows steps of a method used to obtain self normative data for both LBBB and normal sinus beats.

FIG. 11 shows an example of the steps involved in detecting ischemic LBBB and normal sinus beats. In this example, the ST deviation which is the average ST segment voltage minus the PQ segment voltage as calculated for each of any LBBB or normal sinus beats which may exist in the currently sampled data. The resulting ST deviation is then compared to a baseline value calculated from at least one prior period of the data of that patient. Specifically the step 315 is broken down into sub-steps, such as step 3152 where the average ST segment voltage for a normal sinus beat "Vstn" is calculated from the digital data for that beat. Next in step 3154, the average PQ segment voltage for the normal sinus beat "Vpqn" is computed. Next step 3156 calculates the ST deviation for the normal sinus beat "STdn", which is the difference between the ST and PQ average voltages. In step 2158, the ST deviation STdn is compared to a baseline ST Deviation "STdn(b)" calculated from the average ST deviation voltages from a multiplicity of normal sinus beats over a prior time period. For example, the baseline value STdn(b) might be the average of the ST deviation of 24 sets of 8 normal sinus beats collected once per hour each hour for the prior 24 hours. A beat may be classified as ischemic in step 3158 if the beat is shifted by more than a preset ST shift threshold for normal sinus beats, "Vn". In other words, the beat is shifted if the current beat's ST deviation minus the baseline ST deviation is more than the ST shift threshold. This condition is met when STdn−STdn(b)>Vn. It is also envisioned that the threshold can be a set percentage of the baseline signal amplitude for normal sinus beats A(n) which can be the height of the R wave or the peak to peak amplitude of the entire QRS complex. In this case the condition for detection of ST shift would be calculated as:

$$\frac{(STdn - STdn(b))}{A(n)} > Sn$$

where Sn is a percentage. For example Sn might be 20% and if the ST deviation shifts more than 20% of the R height from the baseline data collected over the prior period, then the beat is classified as ischemic.

If the beat is ischemic, step 315 goes on to step 316 where it increments the ischemic normal sinus beat counter i(n) and then on to step 340 of the main loop 300 of FIG. 10. If the beat is not ischemic then step 315 goes to step 317 of the main loop 300 described in FIG. 10.

For LBBB beats the step 322 is broken down into sub-steps including step 3222 where the average ST segment voltage for a LBBB beat Vstp is calculated from the digital data for that beat. Next in step 3224, the average PQ segment voltage for the paced beat Vpqp is computed. Next step 3226 calculates the ST deviation for the paced beat, STdp which is the difference between the ST and PQ average voltages. Then in step 3228, the ST deviation STdp is compared to a baseline ST Deviation STdp(b) calculated from the average ST deviation voltages from a multiplicity of LBBB beats over a prior time period. For example, the baseline value STdp(b) might be the average of the ST deviation of 24 sets of 8 LBBB beats collected once per hour each hour for the prior 24 hours. To see if the beat is ischemic one checks in step 3228 if the beat is shifted by more than a preset ST shift threshold for normal sinus beats, Vp. In other words, the beat is shifted if the current beat's ST deviation minus the baseline ST deviation is more than the ST shift threshold. This condition is met when STdp−STdp(b)>Vp. It is also envisioned that the threshold can be a set percentage of the baseline signal amplitude for normal sinus beats A(p) which can be the height of the R wave or the peak to peak amplitude of the entire QRS complex. In this case the condition for detection of ST shift on LBBB beats would be calculated as $$\frac{(STdp - STdp(b))}{A(p)} > Sp$$

Where Sp is a percentage. For example Sn might be 20% and if the ST deviation shifts more than 20% of the R height from the baseline data collected over the prior period, then the beat is ischemic. When STdp(b) an A(p) are not available, then STdn(b) and A(n) may be used with a correction factor so that LBBB beats may be compared to a normal sinus baseline, with correction for differences expected between the 2 beat types.

If the beat is ischemic, step 322 goes on to step 323 where it increments the ischemic LBBB beat counter i(p) and then on to step 340 of the main loop 300 of FIG. 10. If the beat is not ischemic then step 322 goes to step 330 of the main loop 300 described in FIG. 10.

FIG. 12 shows an example of steps 340, 342 and 350 as follows: In step 340 sub-step 3402 first checks if there are enough normal sinus beats k(n) to perform a detection analysis with step 3408. It does this by comparing k(n) to a preset value K1. If k(n) is not greater than K1 the step 340 continues to step 3404. If k(n) is greater then K1 then sub-step 3408 is initiated to check if there have been enough ischemic beats in the segment to declare the segment of Y seconds of being ischemic. It does this by comparing the number of normal sinus ischemic beats i(n) to a preset threshold for normal sinus beats Tn. If i(n) is not greater than Tn step 340 goes on to step 3404. If i(n) is greater than Tn then the segment is declared to be ischemic by sub-step 3420.

In step 3404 the step 340 sees if there have been a sufficient number of LBBB beats in the segment to declare the segment ischemic based only on LBBB beats. If there are enough LBBB beats where k(p) is greater than the preset value K2, the step 340 continues to step 3412 to see if the segment has enough LBBB beats i(p) to be declared ischemic. If i(p) is greater than the threshold for detecting LBBB beats Tp then step 340 goes to step 3420 and declares the segment to be ischemic. If there are not enough LBBB beats k(p) then step 340 continues on to step 3406 where it checks to see if there are enough combined number of LBBB and normal sinus beats. In step 3406 if the total number of LBBB and normal sinus beats combined k(n)+k(p) is greater than a preset value K3 then the step 340 goes to sub-step 3414 to check if the combination of the number of ischemic normal sinus beats i(n) and LBBB beats i(p) when summed together exceed a preset threshold Tc for combined ischemic beats in a segment. If i(n)+i(p) is greater than Tc then the segment is declared ischemic by sub-step 3420. If i(n)+i(p) is not greater than Tc then step 340 returns to step 308 of the main loop to get the next beat. In step 3406 if the total number of LBBB and normal sinus beats combined k(n)+k(p) is not greater than a preset value K3 then the step 340 goes back to the main loop step 308 to get the next beat.

An example of the execution of this method can require that that K1 and K2 are set to 6 beats and K3 is set at 8 beats. Tn could be 4 beats, Tp could be 5 beats and Tc could be 6 beats. Thus if 4 out of 6 normal sinus beats or 5 out of 6 LBBB beats or 6 out of 8 combined LBBB and normal sinus beats are ischemic then the segment would be declared ischemic in sub-step 3420.

If the segment is declared ischemic by sub-step 3420 of step 340 then step 342 is run to check if there have been enough (e.g. N) ischemic segments in a row to declare that the patient is ischemic and alert the patient. For example N might be 3 segments in a row. Additionally, if the change in a beat feature causes a second threshold (e.g. a second Sn might be set to 50%) is large enough then N may be adaptively adjusted to 1 or 2.

If there have not been enough segments in a row in step 342 then return to step 302 and begin collecting data for the next segment, incrementing a counter to keep track of the current number of successive ischemic segments.

If there have been enough ischemic segments in a row in sub-step 342, then step 350 is initiated to alert the patient or take additional actions. The first check in step 350 is to determine if the ischemia is a recovery event by looking for periods of elevated heart rate in the prior R minutes. In sub-step 352 if there have been more than Q elevated heart rate beats detected in the prior R minutes then sub-step 352 declares that the ischemic event is a recovery type event and initiates a less urgent patient alert or just saves the data for later physician review. For example if more than Q=20 beats in the last R=5 minutes, a recovery event may be detected. In this case, after a less urgent type alert is issued or data is saved, step 350 returns to step 302 of the main loop to get another Y seconds of data. According to one embodiment, the recovery event handling in step 352 is applied only if both all of the current beats and prior high heart rate beats were associated with sinus/atrial rhythm.

Alternatively, if there has not been a prior period of elevated heart rate then the ischemic event may be a heart attack and an emergency alarm is initiated by sub-step 354 to get the patient to immediately seek medical attention. If an Emergency alarm is initiated by step-sub 354, then step 350 may initiate sub-step 358 to begin addition electrogram data storage associated with the detected emergency alarm. For example, electrogram segments of Y seconds of data from the prior 24 hours before the event and the 8 hours after the event might be stored in the memory 118 of the IMD 3' of FIG. 3 for later review. At some time after this tracking is initiated by sub-step 358, the step 350 returns to step 302 to begin collecting Y second long segments of data again. It is envisioned that this period could be the 8 hours of post event data storage. The reason for not immediately restarting detection following an emergency alarm is that there is no need to keep warning the patient and an ischemic event can last, or re-occur, for hours.

FIG. 13 shows a diagram of the process 400 used by an embodiment of the present invention. This embodiment relies on the classification of the state of the heart signal to be in one of three modes. Mode 1 (401) where LBBB beats are rare, Mode 2 (402) where LBBB beats are essentially continuous, and, Mode 3 (403) where the patient has daily episodes of both LBBB and normal sinus beats. FIG. 13 details how the process 400 detects ischemia in the presence of each mode as well as the conditions and process by which the process 400 can change from one mode to another.

In an illustrative example, patient is in Mode 1 at step 401. For this embodiment of the present invention, in Mode 1, LBBB beats are ignored for ischemia detection. For example, in Mode 1, step 310 in FIG. 10, would not go to step 320 if an LBBB beat is detected, but instead would classify the LBBB beat as a bad/rejected beat (and also increment K(p)) and return to step 308 to get the next beat. It would only look for ischemia by following step 314 if the beat is a normal sinus beat identified in step 310. This would affect step 340 of FIGS. 10 and 12 as there would be no LBBB beats counted and only the sub-steps 3402 and 3408 for normal sinus ischemia detection for the segment of Y seconds would operate.

Similarly if the patient is in Mode 2, then operation of step 402 would occur. For this embodiment of the present invention, in Mode 2, normal sinus beats are ignored for ischemia detection. For example, in Mode 2, the step 310 in FIG. 12, would not go to step 312 if a normal sinus beat is detected, but instead would classify the normal sinus beat as a bad/rejected beat and return to step 308 to get the next beat (although K(n) would still be augmented). It would only assess ischemia if the beat is an LBBB beat identified in step 310. This would affect step 340 of FIGS. 10 and 12 as there would be no normal sinus beats counted and only the sub-steps 3404 and 3412 for LBBB beat ischemia detection for the segment of Y seconds would operate.

Of course in Mode 3 503 the full process 300 for both LBBB and normal sinus beats would be operative and neither type would be classified as bad/rejected by the step 310 of FIG. 10.

FIG. 13 provides a first example of how the IMD 3 of FIGS. 1 and 2 might identify changes in the balance of LBBB and normal sinus beats and therefore switch between different detection modes. The processor 100 is configured to identify mode transitions based on the proportion of beats of different beat types, or a change in the proportion of beat types from a prior interval. If the patient is in Mode 1, step 401 then after a D minute delay step 404, the step 405 will check to see if there are enough LBBB beats to warrant a mode change. Step 405 checks to see if there are a lot of LBBB beats, e.g. more than N LBBB beats over a period of M minutes, where N and M could be 50 beats over 10 minutes. If there are not enough LBBB beats, the process 400 returns to Mode 1. If there are enough LBBB beats in step 405, the process 400 then goes to step 406 where it is determined whether there is mostly LBBB beats where for example, more than E % of the beats are paced. E % for example, might be 90%. This would correspond to a condition where the patient's heart would go from rare LBBB beats to almost continuous LBBB beats. If the answer to step 406 is no and there are still a fair number of normal sinus beats, then the process 400 sits in step 414 where it detects ischemia only on normal sinus beats, but will begin collecting LBBB beats to create a LBBB beat baseline so long as the normal sinus beats are looking "normal".

Regarding baseline acquisition, in the aforementioned application entitled "Baseline Processing for the Detection of Cardiac Events," a candidate baseline segment does not qualify as a valid baseline if its average ST segment deviation is too far shifted from the then applicable baseline, which is an average of preceding qualifying baseline segments. Obviously, such a scheme requires a start-up period. In the context of the present invention, startup periods may be required after a switch from Modes 1 or 2, in which case there may not be any valid baselines with which to compare a current segment. In this case, to define an initial baseline, the system may collect W segments over a P hour period (during which normal baseline acquisition will not be attempted) with W and P preferably set to 40 and 4, respectively. The applicable baseline may be set as an average of the ST deviation of these W segments, after eliminating outliers. Normal baseline acquisition may then be performed, using the above mentioned applicable baseline. Initially, candidate baseline segments will be compared against this applicable baseline to determine if they qualify as valid baselines. The new applicable baseline will then be updated as a weighted average of the then applicable baseline and the new valid current baseline segment. The applicable baseline will be updated with subsequent valid baselines. Alternatively, a prior "stale" baseline value may be used, or a best guess baseline may be set by the system (e.g. it may select a baseline that is related to another beat type), and the ischemia detection threshold may be increased to avoid any lack of specificity caused by using a sub-optimized baseline reference value.

According to the above mentioned "Baseline Processing for the Detection of Cardiac Events," a candidate baseline segment does not qualify as a valid baseline if the heart rate is not in the normal range. In the case where a patient experiences heart rate dependent LBBB, such that normal sinus beats tend to occur at normal heart rates and LBBB beats tend to occur at higher heart rates, the heart rate restriction is not applied to LBBB baselines. In other words, a segment that is classified as a LBBB segment at a high heart rate can qualify as a baseline.

After enough LBBB beat baseline data is collected in step 420 that follows step 414, the process will go to step 403 entering Mode 3 where both LBBB and normal sinus beats are checked for ischemia (if step 420 is no then the process reverts to step 414). Alternatively, if the answer is yes to step 406 then there may not be enough normal sinus beats present to detect an ischemic event. If this is so, step 408 will check to see if there is baseline data for LBBB beats that is not too old (i.e. "stale") and is sufficient for detecting ischemia in LBBB beats. If the old baseline is not stale then step 410 will cause the baseline for LBBB beats to become the current baseline and the process 400 will then move to step 403 Mode 3.

If there is no baseline data from a sufficiently recent period then there are three different embodiments (Choices A, B and C) of the present invention which may be operated. In Choice A, step 416 would alert the patient that the mode has changed. This change in the patient's condition may be treated as less urgent alert than an ischemic event but still merits an alert for the patient to see their doctor, for example, to determine if perhaps a change in medication is warranted. In this case, step 420 would then begin collecting LBBB beats to create a baseline for ischemia detection. Once enough LBBB beats are collected, the method 400 then proceeds to step 403 Mode 3.

In Choice B, if non-stale baseline data does not exist as determined in step 408 then in step 418 a different ischemia detection method is selected. In this example, ischemia detection can occur by examining the time rate of change of either ST segment voltage or ST deviation where there is no longer a baseline term incorporated into the ischemia evaluation formula. For example if over a 3 minute moving-window period there is a ST-shift of more than 20% of the current R-wave height that has occurred consistently over a number of segments and this feature remains shifted for an additional 2 minutes, then ischemia could be detected and the process will jump to step 350 where an alarm is provided. Even while running such a time rate of change algorithm, LBBB beats might be collected for a standard baseline where in step 420 after enough are collected, the system can go to step 403 Mode 3 (otherwise it reverts step 406). Even in this instance, in step 420, the detection of ischemia from sinus/normal sinus beats is ongoing if possible.

In Choice C, the existing baseline data for normal sinus beats with a correction or offset is used to provide a temporary baseline that can be used for LBBB beat ischemia detection. For example, the LBBB beat baseline might be some percentage of the normal sinus baseline data for ST deviation and R-wave height or there might be an offset. There are other choices (not shown in FIG. 13) which may occur and these may be available in addition to choices A-C or A-C may be substituted with these. For example, Choice D can include reverting to use of a population based threshold which does not require comparison of the ST-deviation to a self-normative baseline value. Choice E can include using a baseline which is stale as long as certain criteria are met (e.g. the baseline for the subject has been very stable and, for example, has only deviated within +/−1% for the last 4 days) suggesting that this information is still adequate for a comparison.

In Mode 3 403 the process 400 is checking both LBBB and normal sinus beats for ischemia using the entire process 300 of FIGS. 10, 11 and 12. The present invention envisions that in Mode 3 if after a time period of F hours in step 432, there are almost no LBBB beats seen by step 436 then the process would return to Mode 1, 401 where LBBB beats are ignored for ischemia detection.

Similarly if after a period of G hours in step 434 there are almost no normal sinus beats seen by step 438, the process 400 can go to step 402 Mode 2 operation where sinus/normal sinus beats are ignored for ischemia detection.

In both steps 436 and 438 if the answer is no, then the process 400 returns back to Mode 3, 403 where both LBBB and normal sinus beats are examined for ischemia.

FIG. 14 continues the flow chart for the process 400 showing how the process 400 moves out of Mode 2 with nearly continuous LBBB beats into Mode 3. The process 400, as shown, cannot go from either Mode 1 to Mode 2 or Mode 2 to Mode 1 without first passing through Mode 3. While a direct transition from Model to Mode 2 is obviously possible, skipping Mode 3 could cause periods where ischemia cannot be measured accurately if there is not a good LBBB baseline. FIG. 13 already shows how the process 400 transitions from Mode 1 to Mode 3, and how Mode 3 goes back to Modes 1 and 2. In FIG. 14, if the patient has continuous LBBB beats, it is conceived that the heart could at some point change to have a large number of sinus/normal sinus beats.

While in Mode 2, 402 the process 400 would go to step 452 and wait D' minutes and then check to see if there have been a large number of normal sinus beats in step 454. For example step 454 might look to see if there have been N' normal sinus beats in M' minutes where N' and M' could be 50 beats over 10 minutes. If the condition of step 454 is not met, the process 400 returns to step 402 then 452 to wait another D' minutes where D' for example could be 5 minutes. Step 402 is active while block 452 is in effect so that detection in Mode 2 is not stopped while waiting time D'. If the condition of step 454 is met and there are a sufficient number of normal sinus beats the step 456 checks to see if there are mostly normal sinus beats with more than E'% of the beats in the last M' minutes being sinus where for example E' might be 90%. If there are less than this number of normal sinus beats but still enough to have met the condition of step 454 then the process 400 will detect ischemia only on LBBB beats until it has enough time and normal sinus beats to develop a sinus beat baseline in step 457. Methods for establishing baselines were described with respect to step 414 of FIG. 13). Once a baseline has been established, the process 400 will go to step 403 which is Mode 3 where detection of ischemia looks at both LBBB and normal sinus beats as shown in the example of FIGS. 10 through 12.

If the condition of step 456 is yes in step 458 checks to see if there is older baseline data for normal sinus beats that is still usable/good. Again, in an alternate embodiment, cardiac memory also plays a role in the baseline validity determination. If so that baseline is then enabled for ischemia detection in step 460 and the process 400 goes to step 403 for Mode 3 detection. If there is not a usable baseline for normal sinus beats, step 458 then moves to one of 3 embodiments or choices 462, 464 and 466. These choices are:

Choice 1, 462—while collecting normal sinus beat data to form a usable baseline determined by step 480, monitor normal sinus beats for ischemia using a different algorithm for example, look at the time rate of change of ST segment deviation analogous to the manner described with reference to step 418 of FIG. 13.

Choice 2, 466—there may be strong similarities to the changes in both LBBB and normal sinus beats due to ischemic conditions that would allow the LBBB baseline to be used to calculate an approximate normal sinus baseline for ischemia detection. For example, the threshold for detection of an ischemic LBBB beat might be 25% of the baseline R height, and 25% for ischemic normal sinus beats. The average ST shift over the last hour for LBBB beat ST deviation as compared to the LBBB baseline ST deviation might be 10% of the baseline R height. One could then assume that for normal sinus beats the current average ST shift is also 10% and therefore calculate what the normal sinus baseline ST deviation would be based on LBBB beat data and current measures of ST deviation for normal sinus beats. This technique could be used while continuing to collect normal sinus beats to create a usable baseline. Once step 380 determines that such a usable baseline exists, the process 400 goes to step 403 for Mode 3 operation. Alternatively, if for example; the threshold for detection of an ischemic LBBB beat might be 35% of the baseline R height, and 25% for ischemic normal sinus beats, then a correction factor can be used which adjusts either the threshold or the feature being compared to the threshold.

Each of these 2 choices could work to allow the process 400 to still protect the patient by detecting significant electrogram changes indicative of heart attack even though there is not a usable baseline for normal sinus beats. When a usable baseline occurs then Mode 3 can be entered and from Mode 3 the process 400 may revert to either Mode 1 or Mode 2, according to the composition of LBBB and normal sinus beats which are then subsequently acquired.

FIG. 15 shows steps of a method 500 used to classify beats as normal beats, LBBB beats or other type beats. The method will be described in connection with FIGS. 16a and 16b, which show fiducial markers associated with the amplitude and slope respectively of normal sinus and LBBB QRS complexes. The method of FIG. 15 will be described with respect to a particular, and relatively normal, QRS morphology associated with the electrogram from the right ventricular apex (with a can-to-tip polarity). This morphology comprises an initial downstroke (Q) in FIG. 16a followed by an upstroke (R) in FIG. 16a, followed by a terminal downstroke (S) in FIG. 16a. Due to patient specific factors, the "QRS" complex may lack a Q wave or otherwise have a shape that varies significantly from that shown in FIG. 15a. The modification of the method 500 for patients whose normal "QRS" does not exhibit a Q wave will be described below. Furthermore, the method 500 is preferably applied to beats that have been screened by an R-R interval based test to detect PVC's and aberrant beats.

Figures 16A, 16B:
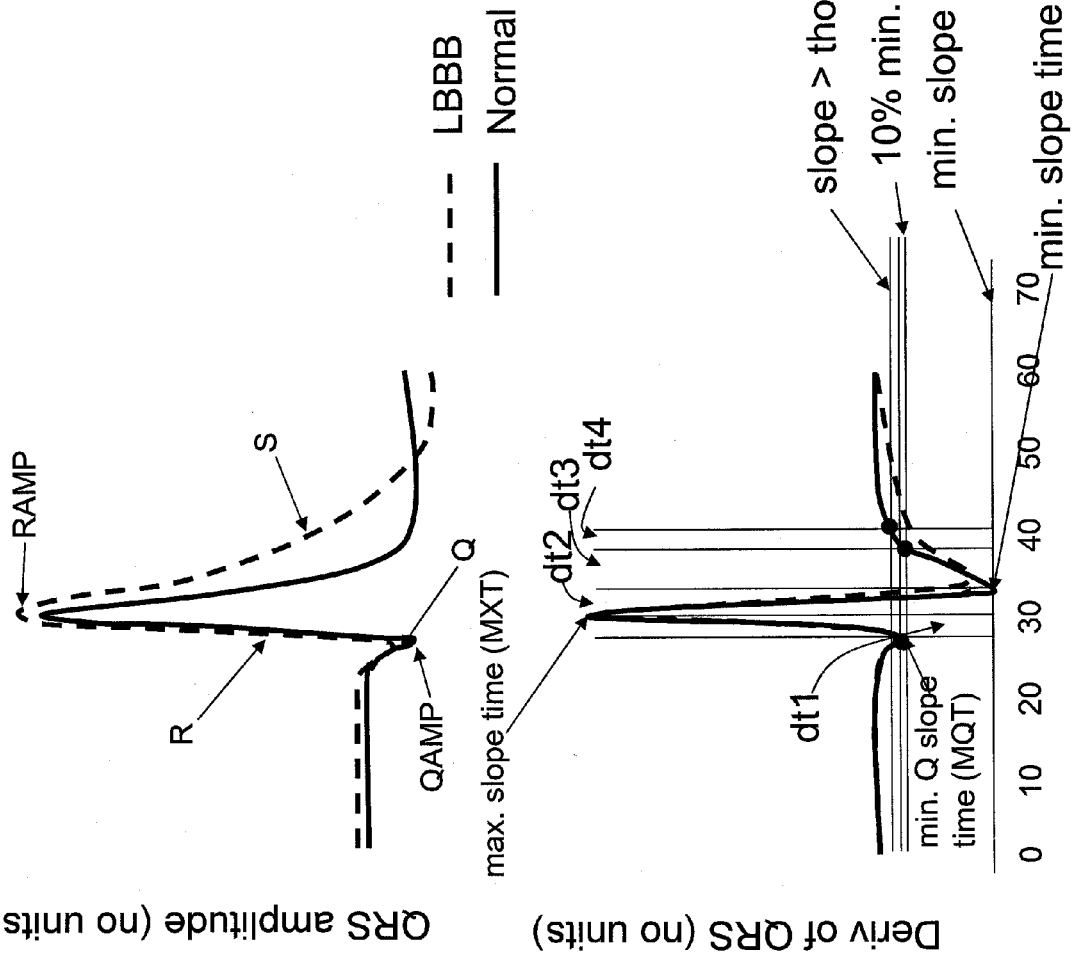
FIG. 16a shows normal and LBBB QRS complexes marked with fiducial points used to classify beats.
FIG. 16b shows corresponding slopes of normal and LBBB QRS complexes marked with fiducial points used to classify beats.

In step 502, the amplitude and slope of the initial Q wave are examined. The Q wave amplitude (QAMP) in FIG. 16a is determined by finding the maximum (negative) amplitude between the first two points after a prior beat that satisfy peak detection slope criteria. An amplitude test is satisfied if the amplitude is within a programmable percentage of the expected value, which is a programmable fraction of the baseline signal amplitude collected as part of the routines described with respect to FIGS. 5, 6 and 13. An exemplary value of the programmable percentage is 20%. The method 500 operates in Mode 1 (see FIG. 13), according to which a good baseline for normal beats is available. If the device operates in Mode 2, in which LBBB are common, the method 500 is preferably modified by applying the baseline signal amplitude of LBBB beats rather than normal beats.

In an alternative embodiment, the QAMP expected value is an exponential average that is updated with each QAMP value that falls within the +/−20% threshold. The same +/−20% test and expected value scheme is applied to the min Q slope (shown in FIG. 16b). In the aforementioned baseline acquisition methods, the min. Q slope for baseline beats is determined and stored.

If a patient's normal QRS complex lacks a Q wave, step 502 is omitted, and a QRS onset point is determined according to slope criteria. Alternatively, for patients lacking a Q wave, QRS onset can be determined according to the methods described in U.S. patent application Ser. No. 12/721,836, filed Mar. 11, 2010, assigned to the assignee hereof, entitled "QRS ONSET AND OFFSET DETECTION WITH ADAPTIVE TEMPORAL WINDOWING," which is incorporated by reference herein.

Returning to step 502 in the case where a Q wave is normally present, if either the amplitude or slope tests fail, the beat is neither normal nor LBBB and is either tagged as "unknown" or further classified in block 512. If both the amplitude and slope tests pass, control transfers to step 504, which checks the upstroke timing, amplitude and maximum slope. The same +/−20% test and expected value scheme described with respect to block 502 is applied to both RAMP (FIG. 16a) and the maximum slope (FIG. 16b).

In addition, the timing between the minimum Q slope and maximum (R) slope is determined. This time is labeled as dt1 (=MXT−MQT) in FIG. 16b. A duration test is satisfied if this duration (dt1) is within +/− a programmable duration of an expected value, which is determined and stored as part of baseline beat acquisition. An exemplary value of the programmable duration is 10 ms. In an alternative embodiment, the duration expected value is an exponential average that is updated with each dt1 value that falls within the +/−20 ms (using the exemplary duration) threshold. In an alternative embodiment, a test is applied to the timing between RAMP and QAMP.

If any of the above 3 tests fails, control transfers to block 512. Otherwise, control transfers to step 506, which checks the downstroke timing, minimum slope and the ratio of the (previously determined) maximum slope to the minimum slope. The downstroke timing (dt2) in FIG. 16b is the interval between the minimum slope time (MST) and the maximum slope time (MXT). The same duration test described with respect to step 504 is applied in step 506 to duration dt2.

The slope ratio test is whether the ratio of the max/min slopes is +/− a programmable percentage of the expected value. An exemplary value of the programmable percentage is 30%.

If all of the aforementioned tests are positive, control transfers to block 507, which applies tests to timing of the return to baseline (low slope) from the MST is within the normal range. There are two aspects to this test: (1) the duration (dt3) between MST and the time the slope reaches 10% of the value of MST; and (2) the duration (dt4) between MST and the time the slope reaches a specified value (thold in FIG. 16b), which is a preferably programmable percentage of the baseline signal amplitude. Again, the expected durations for both dt3 and dt4 are preferably determined during baseline acquisition. In an alternative embodiment, they are updated according to exponential averages. Both dt3 and dt4 must fall within +/− a programmable duration of the expected values of these variables. If so, the beat is classified as normal in step 508.

Otherwise, control transfers to step 510, to which control also transfers if any of the step 506 tests fail. Step 510 applies the same tests as step 507 except that it uses the expected values for LBBB beats. If LBBB beats have been collected within the last week, the dt3 and dt4 expected values are derived from these beats. Otherwise, the expected dt3 and dt4 values are set to programmable defaults, and a more lenient programmable duration is applied. For example, if the programmable tolerance in the case where recent LBBB data is available is +/−10 ms, then the programmable tolerance in the case where default dt3 and dt4 times are used may be set to +/−30 ms.

In the preferred embodiment, if both of the step 510 tests pass, control transfers to step 516, which classifies the beat as LBBB. Otherwise, control transfers to step 512. In an alternative embodiment, T wave polarity is also checked in block 514 to ensure that the beat is an LBBB beat.

Some of the steps in figures can occur earlier or later than are shown, steps can also be repeated, and steps may also be omitted altogether. The steps of the particular methods shown here can be incorporated into variants of other methods which are shown. Various other modifications, adaptations, and alternative designs are of course possible in light of the above teachings. Therefore, it should be understood at this time that, within the scope of the appended claims, the invention can be practiced otherwise than as specifically described herein.

We claim:

1. A cardiac monitoring device configured to analyze electrical signals from the heart to detect ischemic events, including:
   at least one sensor designed to collect the electrical signal from the heart;
   electrical circuitry coupled to the sensor and configured to amplify and digitize the electrical signal to produce sensed data;
   memory storage coupled to the electrical circuitry to store the sensed data;
   a processor configured to:
      analyze the sensed data in the memory storage;
      based on the sensed data, distinguish between sinus beats, left bundle branch block beats and other types of beats, and measure at least one feature of beats associated with sinus beats and left bundle branch block beats during a predetermined time interval, respectively; and
      detect the presence or absence of an ischemic event by applying a first ischemia detection criterion to the sinus beat measured feature and a second ischemia detection criterion to the left bundle branch block measured feature dependent upon a number of sinus beats and left bundle branch block beats during said predetermined time interval;
   wherein (1) when said number of left bundle branch block beats are less than a first threshold value, then apply said first ischemia detection criterion to said sinus beat measured feature, (2) when said number of left bundle branch block beats are greater than a second threshold value, then apply said second ischemia detection criterion to said left bundle branch block measured feature, and (3) when said number of left bundle branch block beats and said sinus beats are greater than a third threshold value, respectively then apply said first and second ischemic detection criteria to both said left bundle branch block measured feature and said sinus beat measured feature.

2. The device of claim 1, wherein the processor is configured to distinguish other types of beats from both sinus and left bundle branch block beats by computing the value of a heart signal parameter associated with an early portion of a QRS complex and comparing the value of the heart signal parameter to an expected value that applies to both sinus and left bundle branch beats.

3. The device of claim 2 wherein the heart signal parameter is a function of one of: Q wave amplitude, Q wave slope, R wave amplitude, R wave slope, or duration between the Q and R waves.

4. The device of claim 1, wherein the processor is configured to distinguish between sinus and left bundle branch block beats by computing the value of a heart signal parameter associated with a late portion of a QRS complex and comparing the value of the heart signal parameter to an expected value that applies to sinus beats exclusively or left bundle branch beats exclusively.

5. The device of claim 4 wherein the heart signal parameter is a function of one of: S wave slope, ratio of S wave slope to R wave slope, duration between the R and S waves, or duration of the S wave.

6. The device of claim 5 wherein the duration of the S wave is a function of the time between the minimum slope of the S wave and the time the QRS slope reaches a threshold.

7. The device of claim 6 wherein the threshold is a specified percentage of the minimum S wave slope.

8. The device of claim 6 wherein the threshold is a specified percentage of a measure of signal amplitude.

9. The device of claim 1, wherein an ischemic event is detected when the number of detected ischemic beats which occur within a time interval exceeds a pre-set threshold.

10. The device of claim 1, wherein a calculation performed upon detected ischemic beats which occurred within an interval of sensed data is used to score the interval in relation to detection of medically relevant ischemic event.

11. The device of claim 1, wherein the processor is configured to detect an ischemic event only when a sufficient number beats of sinus or left bundle branch block beats exist within a specified interval.

12. The device of claim 1, wherein the measured feature associated with sinus beats is the same as the measured feature associated with left bundle branch beats.

13. The device of claim 12 wherein the measured feature pertains to ST-segment amplitude.

14. The device of claim 1, wherein at least one of the ischemia detection criteria is modified as a function of heart rate.

15. The device of claim 1, wherein the processor is configured to apply the first ischemia detection criteria for sinus beats by evaluating the difference between the sinus beat measured feature and a reference value calculated for sinus beats.

16. The device of claim 1, wherein the processor is configured to apply the first ischemia detection criteria for left bundle branch beats by evaluating the difference between the left bundle branch beat measured feature and a reference value calculated for left bundle branch beats.

17. The device of claim 1, further containing alerting means for alerting when ischemic events are detected.

18. The device of claim 1 further comprising a wireless communication subsystem coupled to the processor, wherein the processor is configured to activate the wireless communication system upon detecting an ischemic event.

19. The device of claim 1 wherein the processor is further configured to collect data from the digital signals for sinus beats and left bundle branch block beats and to derive corresponding reference baselines of the measured feature for sinus beats and the measured feature for left bundle branch block beats, and wherein the ischemia criteria for sinus beats and left bundle branch block beats are based at least in part on the reference baselines for the sinus beats and left bundle branch block beats, respectively.

20. The device of claim 1 wherein the processor is further configured to collect data from the digital signals for sinus beats and left bundle branch block beats and to derive corresponding reference data of the measured feature for sinus beats and the measured feature for left bundle branch block beats, and wherein the ischemia criteria for sinus beats and left bundle branch block beats are based at least in part on the reference data for the sinus beats and left bundle branch block beats, respectively.

* * * * *